United States Patent
O'Reilly et al.

(10) Patent No.: US 9,259,259 B2
(45) Date of Patent: Feb. 16, 2016

(54) METHOD AND APPARATUS FOR ORTHOPEDIC FIXATION

(71) Applicant: Biomet Manufacturing, LLC, Warsaw, IN (US)

(72) Inventors: Joseph Michael O'Reilly, Granger, IN (US); Philip Harris Frank, Maplewood, NJ (US); Nicholas Joseph Bender, Lake Hiawatha, NJ (US); Michael Charles Strycharz, Kingsport, TN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/753,082

(22) Filed: Jan. 29, 2013

(65) Prior Publication Data

US 2013/0144303 A1 Jun. 6, 2013

Related U.S. Application Data

(63) Continuation of application No. 12/519,212, filed as application No. PCT/US2008/008178 on Oct. 16, 2008, now Pat. No. 8,394,103.

(60) Provisional application No. 60/980,302, filed on Oct. 16, 2007, provisional application No. 60/980,305, filed on Oct. 16, 2007, provisional application No. 61/033,443, filed on Mar. 4, 2008.

(51) Int. Cl.
| | | |
|---|---|---|
| *A61B 17/88* | (2006.01) | |
| *A61B 17/16* | (2006.01) | |
| *A61B 17/17* | (2006.01) | |
| *A61B 17/84* | (2006.01) | |
| *A61B 17/86* | (2006.01) | |
| *A61B 17/92* | (2006.01) | |
| *A61B 19/00* | (2006.01) | |

(52) U.S. Cl.
CPC ......... *A61B 17/8897* (2013.01); *A61B 17/1615* (2013.01); *A61B 17/1703* (2013.01); *A61B 17/1721* (2013.01); *A61B 17/8886* (2013.01); *A61B 17/1668* (2013.01); *A61B 17/848* (2013.01); *A61B 17/864* (2013.01); *A61B 17/92* (2013.01); *A61B 2019/304* (2013.01); *A61B 2019/444* (2013.01); *A61B 2019/462* (2013.01)

(58) Field of Classification Search
CPC ............... A61B 17/88; A61B 17/8897; A61B 17/1615; A61B 17/1721; A61B 17/8886
USPC .................. 606/67, 68, 86 R, 87–89, 95–99, 606/102–104
See application file for complete search history.

(56) References Cited

U.S. PATENT DOCUMENTS

| 4,450,835 | A | * | 5/1984 | Asnis et al. | ...................... 606/96 |
| 5,180,388 | A | * | 1/1993 | DiCarlo | ........................... 606/60 |
| 2002/0058949 | A1 | * | 5/2002 | Iaia | .................. 606/98 |
| 2004/0059329 | A1 | * | 3/2004 | Zander | ............................ 606/53 |

* cited by examiner

*Primary Examiner* — Christopher Beccia
(74) *Attorney, Agent, or Firm* — Schwegman Lundberg & Woessner, P.A.

(57) ABSTRACT

A dual reconstructive wire system for use with an anatomy can include a first guide wire, a second guide wire, a first guide instrument, a first cannulated insertion instrument, and a second cannulated insertion instrument. The first guide wire can pass through the first cannulated insertion instrument such that a first end and a second end of the first guide wire extends beyond the first end and the second end, respectively of the first cannulated insertion instrument. The second guide wire can pass through the second cannulation insertion instrument such that a first end and a second end of the second guide wire extends beyond the first end and the second end, respectively of the second cannulated insertion instrument.

19 Claims, 24 Drawing Sheets

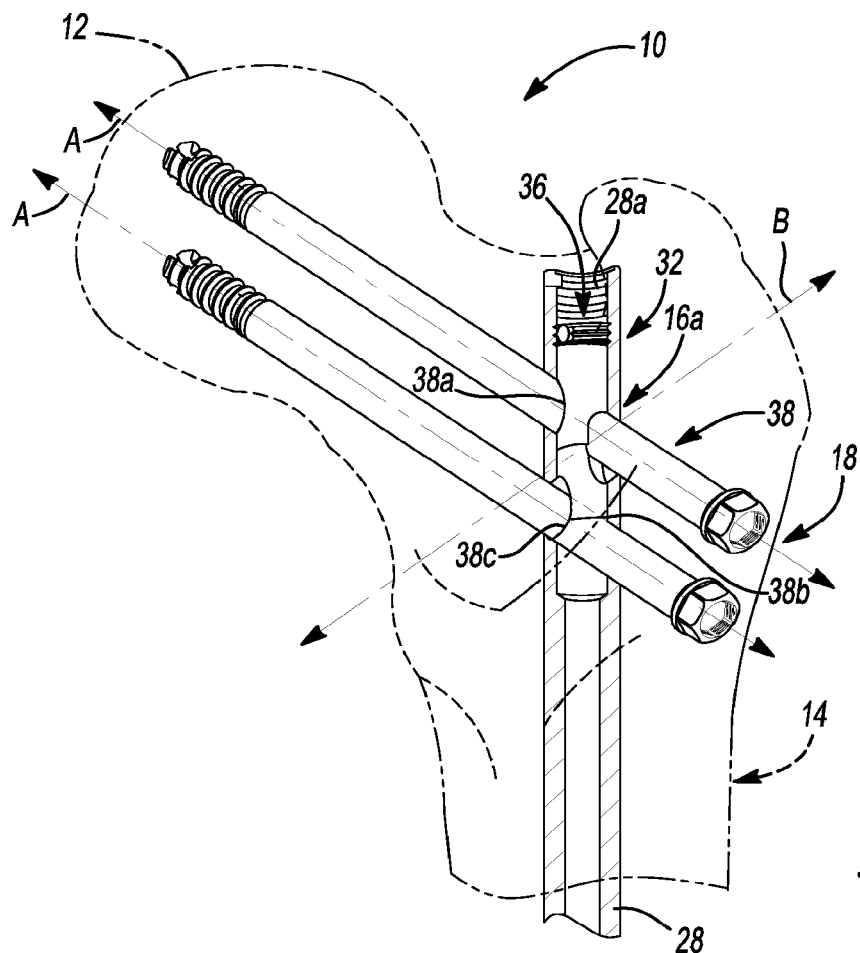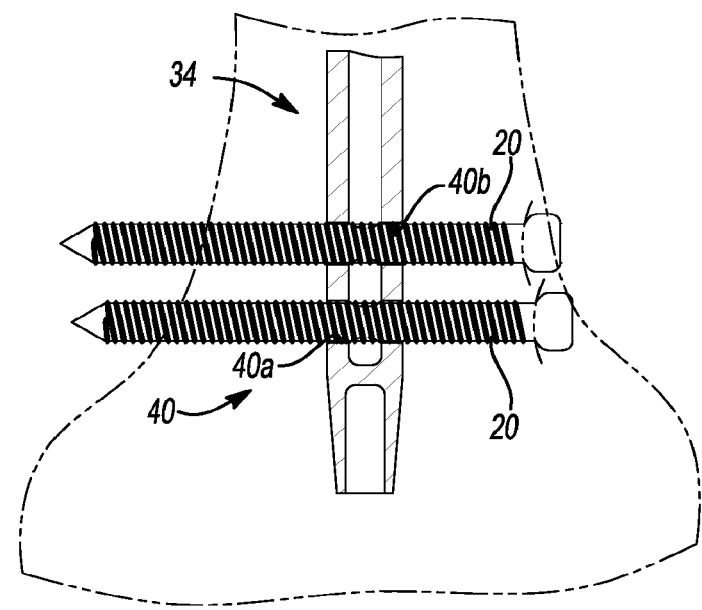
Fig-1

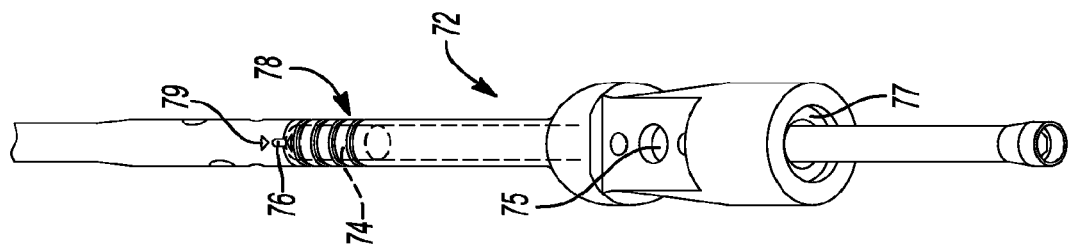
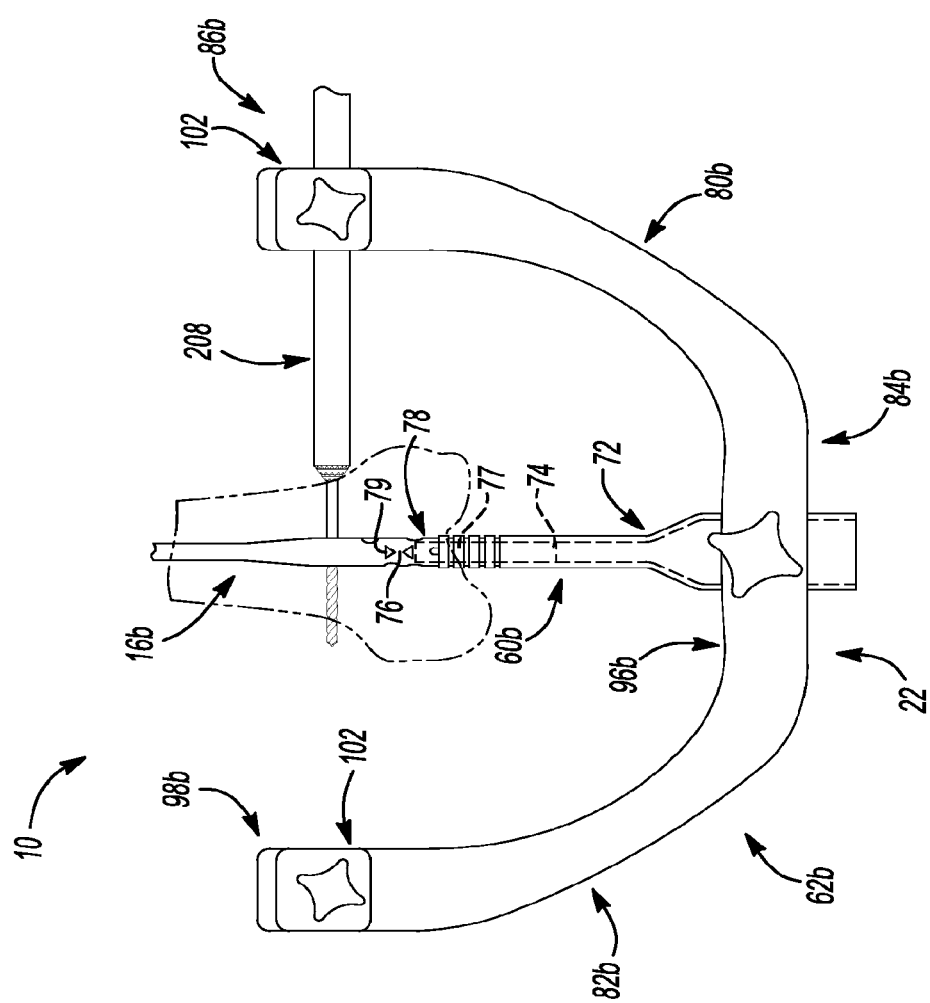

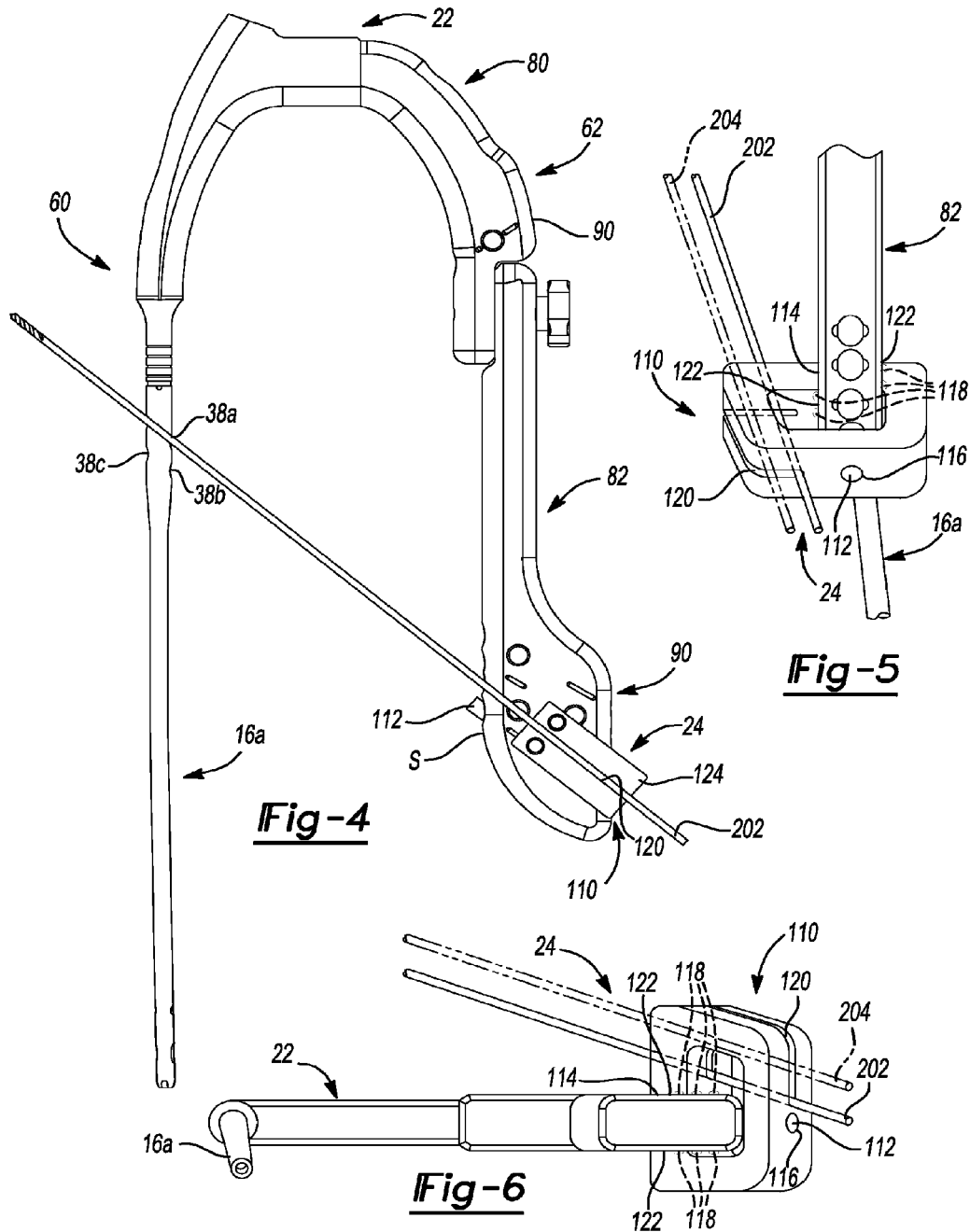

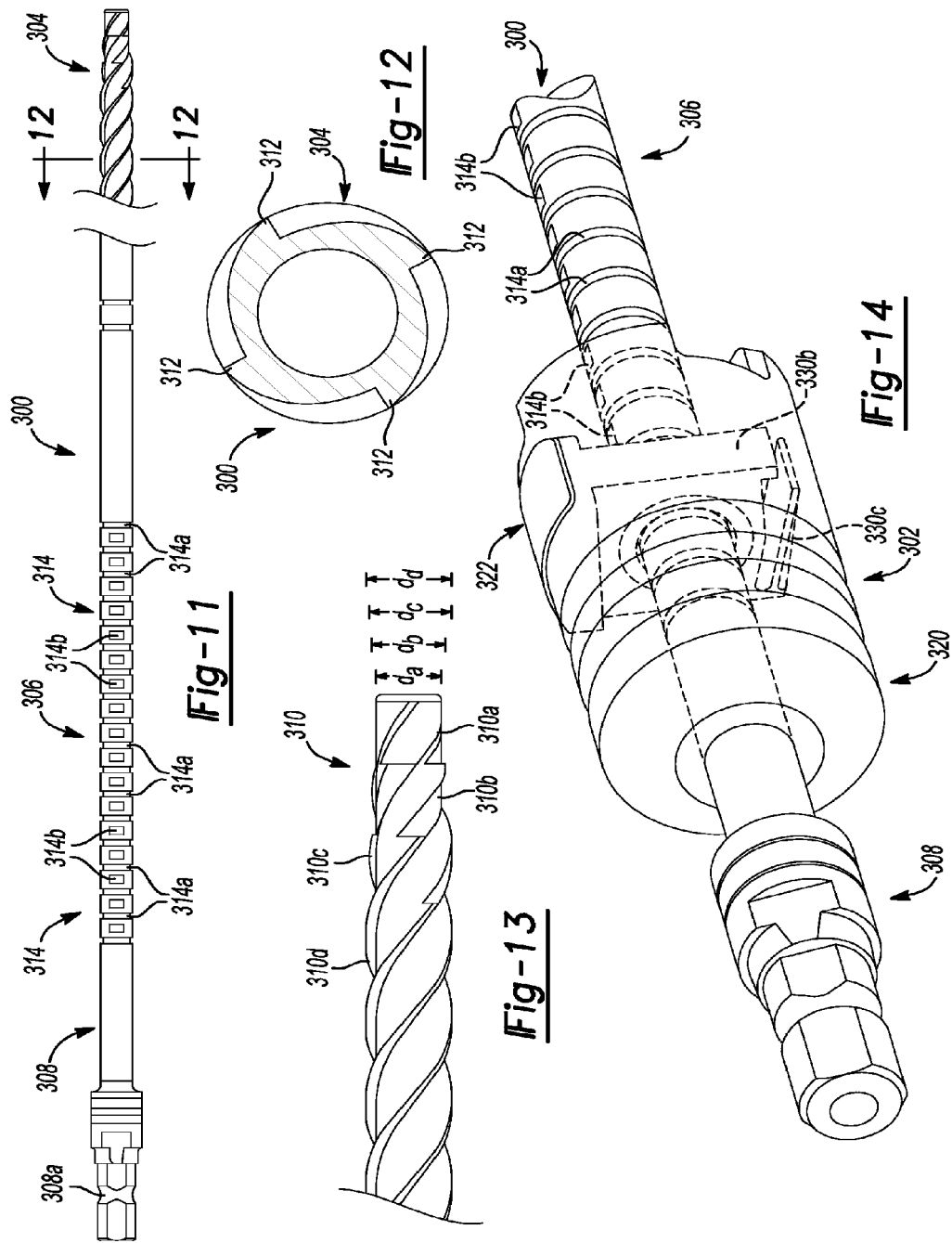

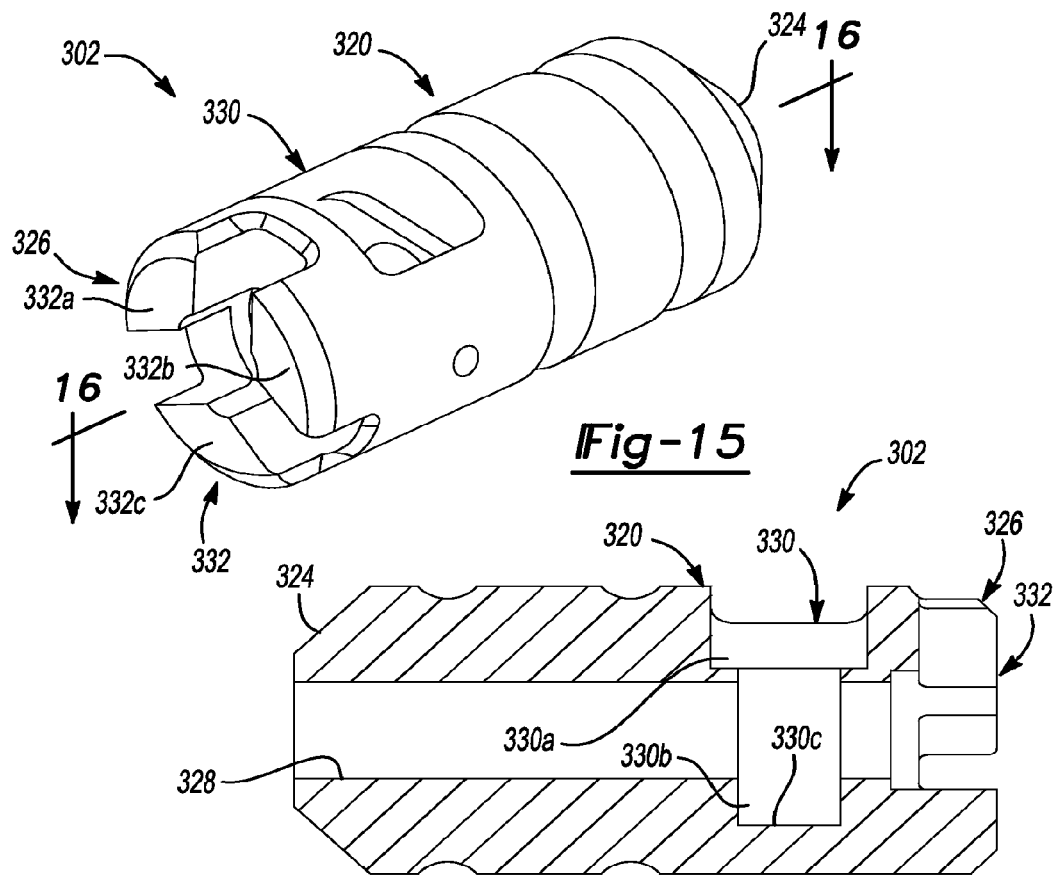
Fig-15
Fig-16
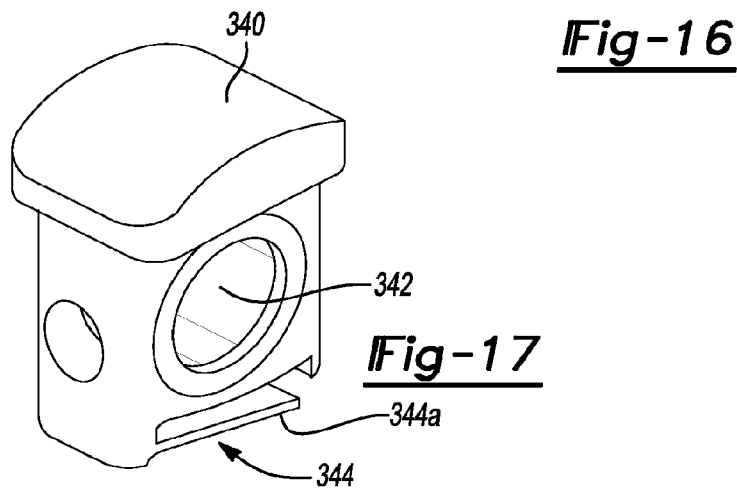
Fig-17

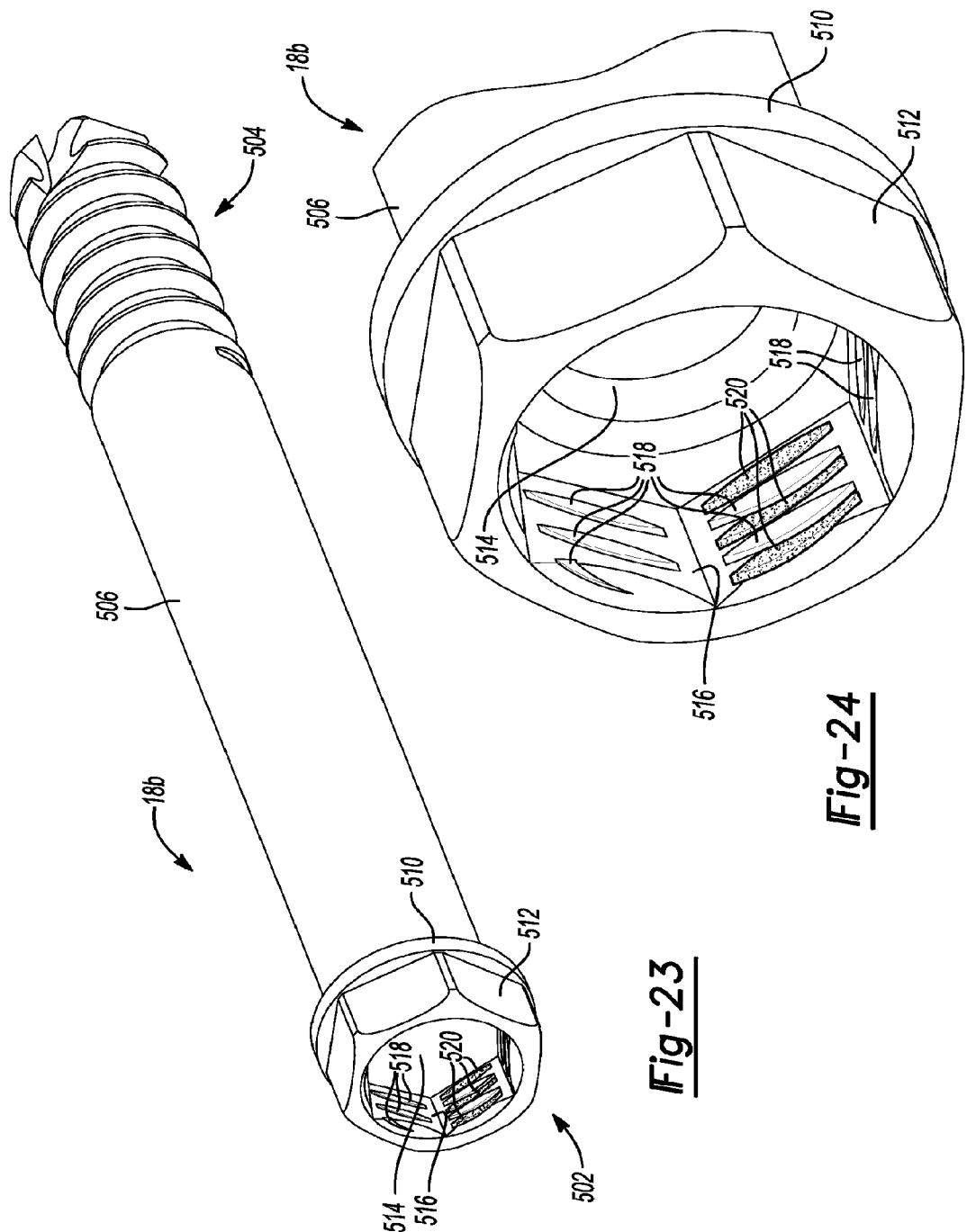

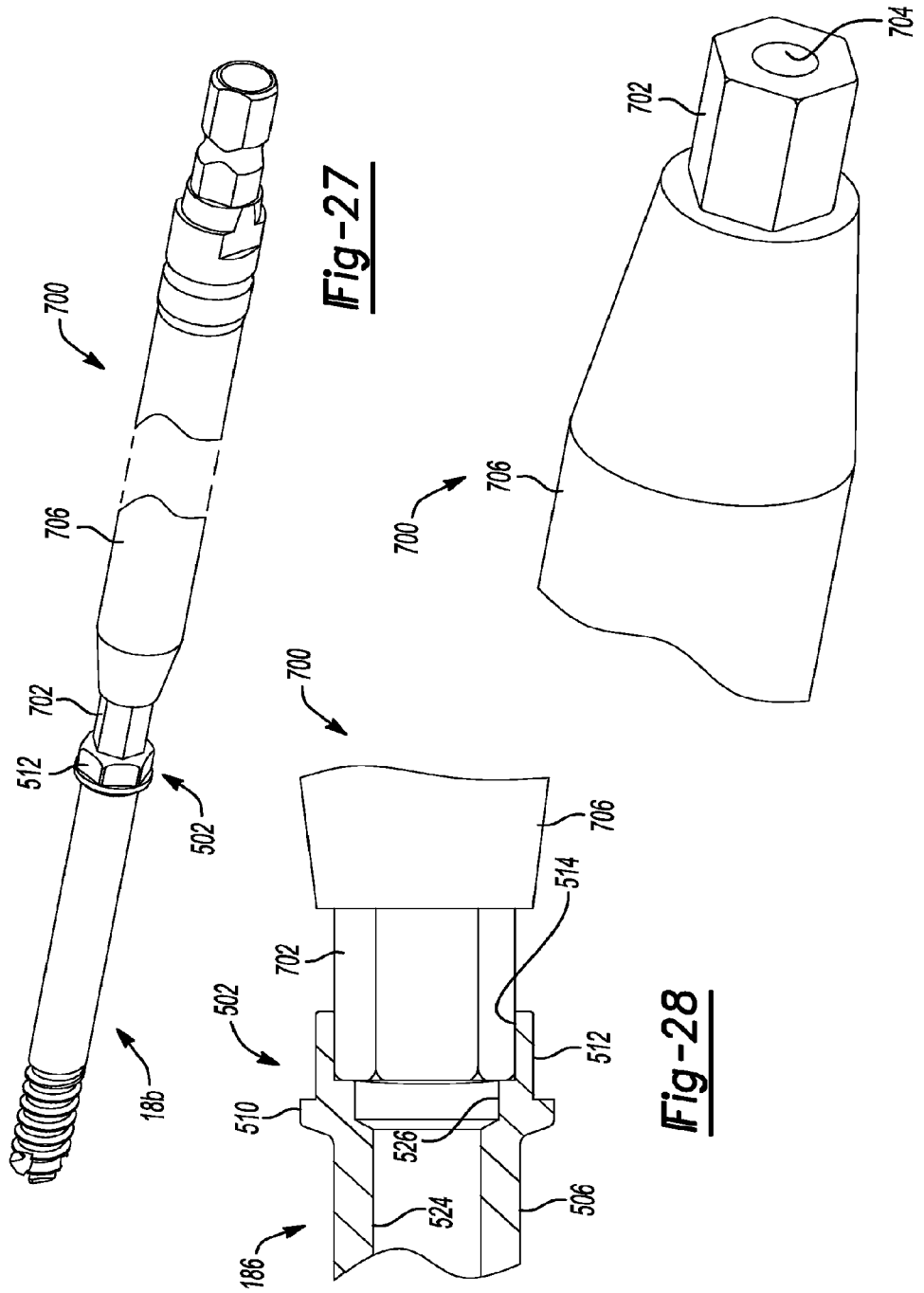

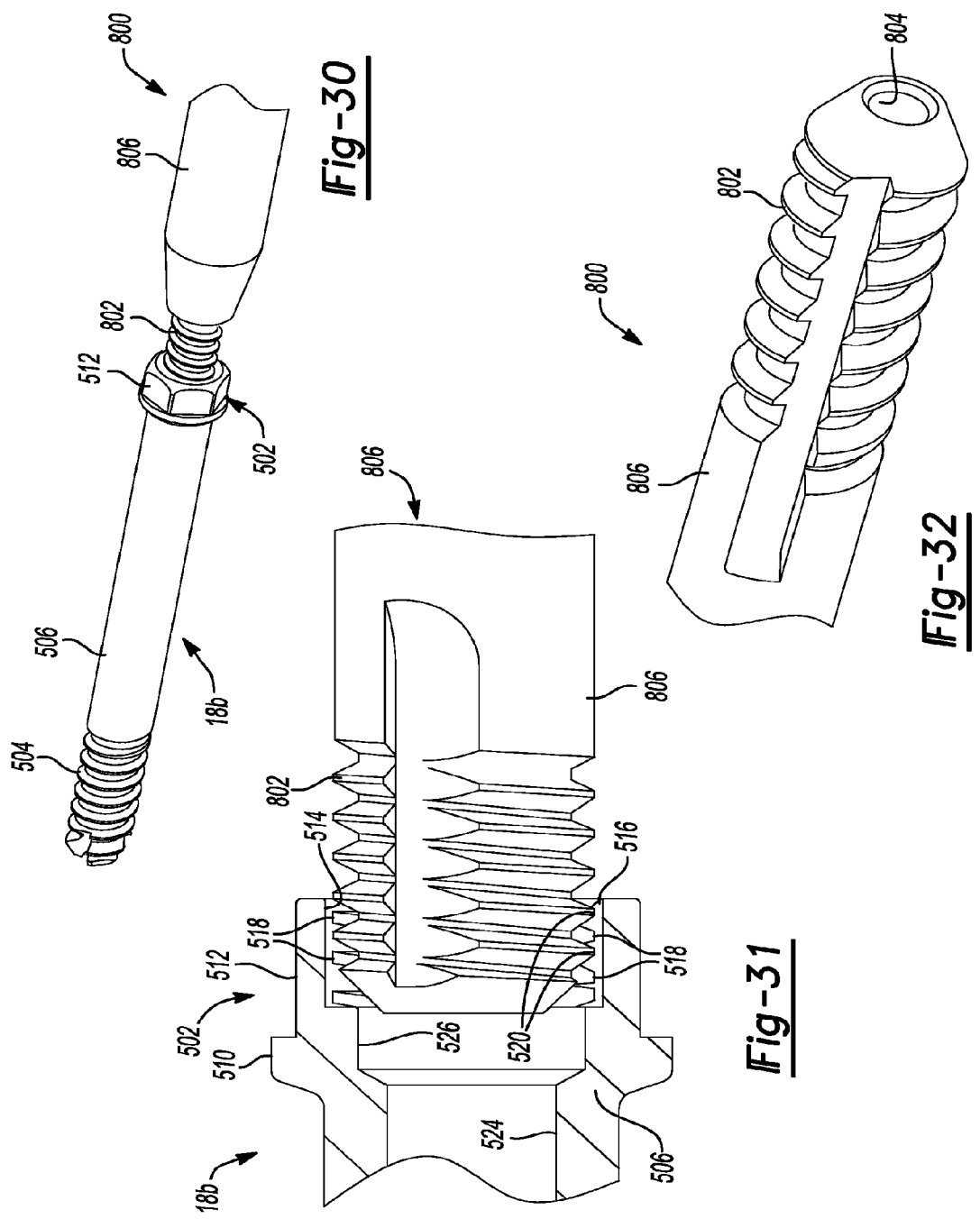

METHOD AND APPARATUS FOR ORTHOPEDIC FIXATION

CROSS-REFERENCE TO RELATED APPLICATIONS

This application is a continuation of U.S. patent application Ser. No. 12/519,212 filed on Dec. 17, 2009, now issued as U.S. Pat. No. 8,394,103, which is a National Stage of PCT/US2008/08178 filed on Oct. 16, 2008. The National Stage application takes priority from U.S. Patent Application No. 60/980,302 filed on Oct. 16, 2007, the disclosure of which is incorporated herein by reference. The National Stage application also takes priority from U.S. Patent Application No. 60/980,305 filed on Oct. 16, 2007, which is incorporated herein by reference. Further, this the National Stage application takes priority from U.S. Patent Application No. 61/033,443 filed on Mar. 4, 2008, which is incorporated herein by reference.

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue, which can require the use of one or more orthopedic fastening features, such as orthopedic nails, screws, etc., to secure the damaged tissue.

For example, in the case of a hip fracture, a femoral nail and one or more orthopedic screws can be used to couple a femoral head to a femur. Generally, in order to properly position the one or more orthopedic screws into an anatomy, a guide and one or more reconstructive guide wires can be used to guide one or more instruments, and/or the associated orthopedic screw, into the anatomy.

The present teachings provide one or more surgical instruments for repairing damaged tissue, such as in the case of a hip fracture. The present teachings can also provide one or more orthopedic screws that can be inserted in and/or removed from bone using any of a dedicated driver or any of commonly available drivers. The present teachings can further provide a surgical instrument for dual reconstructive wires and associated method, among other instruments and methods for repairing a hip fracture.

SUMMARY

A dual reconstructive wire system for use with an anatomy can include a first guide wire, a second guide wire, a first guide instrument, a first cannulated insertion instrument, and a second cannulated insertion instrument. The first guide wire can pass through the first cannulated insertion instrument such that a first end and a second end of the first guide wire extends beyond the first end and the second end, respectively of the first cannulated insertion instrument. The second guide wire can pass through the second cannulation insertion instrument such that a first end and a second end of the second guide wire extends beyond the first end and the second end, respectively of the second cannulated insertion instrument.

The first guide wire can have a first end and a second end. The first end of the guide wire can be operable to engage the anatomy. The second end can extend outside the anatomy. The second guide wire can have a first end and a second end. The first end of the second guide wire can be operable to engage the anatomy. The second end can extend outside the anatomy. The first guide instrument can have an intramedullary nail engagement feature and a guide that defines a first aperture and a second aperture. The first cannulated insertion instrument can have a first end configured to be inserted into the anatomy. The first cannulated insertion instrument can have a second end configured to extend beyond the anatomy. At least a portion of the first cannulated insertion instrument can be received through one of the first aperture or the second aperture. The second cannulated insertion instrument can have a first end configured to be inserted into the anatomy. The second cannulated insertion instrument can have a second end configured to extend beyond the anatomy, with at least a portion of the second cannulated instrument received through the other of the first aperture or the second aperture. The first guide wire can pass through the first cannulated insertion instrument such that the first end and the second end of the first guide wire extend beyond the first end and the second end, respectively, of the first cannulated insertion instrument. The second guide wire can pass through the second cannulated insertion instrument such that the first end and the second end of the second guide wire can extend beyond the first end and the second end, respectively, of the second cannulated insertion instrument.

The guide can further comprise a first arm having a proximate end including the intramedullary nail engagement feature therein and a distal end. The guide can further include a second arm coupled to the distal end of the first arm and that defining the first and second apertures. The guide can further define a third aperture and a fourth aperture. The system can further comprise a fastener that removably couples the first and second arms. The first guide wire can have a colored coating that visually distinguishes the first guide wire from the second guide wire.

According to other features, the system can further comprise at least one radio-opaque marker disposed in the guide. The first guide instrument can be substantially L-shaped and configured to engage an antegrade intramedullary nail. According to other features, the first guide instrument can be substantially U-shaped and configured to engage a retrograde intramedullary nail. The first cannulated insertion instrument and the second cannulated insertion instrument can each include a trocar and at least two soft tissue sleeves.

According to other features, at least one of the two soft tissue sleeves can have a stop contacting the first guide instrument. The trocar can be operable to penetrate a soft tissue of the anatomy. A first one of the two soft tissue sleeves can be slidable over the trocar and have a diameter that is larger than the trocar to create a passageway through the anatomy. A second one of the two soft tissue sleeves can have a second diameter that is larger than the diameter of the first two soft tissue sleeves. The second one of the soft tissue sleeves can be slidable over the first one of the two soft tissue sleeves to create the diameter of the passageway formed by the first soft tissue sleeves in the anatomy. The passageway formed by the first soft tissue sleeve through the soft tissue can terminate adjacent to boney tissue in the anatomy.

According to other features, the system can further comprise a gage including a first scale and a second scale and that can define a single bore. The single bore can receive the second end of the first guide wire, which extends beyond the first cannulated insertion instrument to measure a depth of the first guide wire within the anatomy with the first scale. The gage can receive the second end of the second guide wire, which extends beyond the second cannulated insertion instrument to measure a depth of the second guide wire within the anatomy with the second scale. According to additional features, the system can further comprise a second guide instrument including a post coupling the second guide instrument to one of the first aperture or the second aperture and defining a slot for receipt of at least one of the first guide wire and the second guide wire to verify the alignment of the first guide instrument with the anatomy. The first cannulated insertion instrument and the second cannulated insertion instrument can each include a stop mating with the first guide instrument to limit advancement of the first cannulated instrument and the second cannulated instrument through the first aperture and the second aperture, respectively.

A dual reconstructive wire system for use with an anatomy can comprise a first wire having a first end and a second end. The first end of the first guide wire can be operable to engage the anatomy. The second end operable to extend outside the anatomy. A second guide wire can have a first end and a second end. The first end of the second guide wire can be operable to engage the anatomy. The second end can be operable to extend outside the anatomy. The first U-shaped guide instrument can have an intramedullary nail engagement feature on a first end and a guide on an opposite end. The guide can define a first aperture and a second aperture. The first U-shaped guide instrument can include two independent and selectively attachable arms. A first cannulated insertion instrument can have a first end that is operable to be inserted into the anatomy with at least a portion of the first cannulated insertion instrument received through one of the first aperture or the second aperture. A second cannulated insertion instrument can have a first end operable to be inserted into the anatomy with at least a portion of the second cannulated insertion instrument received through the other of the first aperture or the second aperture.

According to other features, the first guide wire can pass through the first cannulated insertion instrument such that the first end and the second end of the first guide wire extend beyond the first end and the second end, respectively, of the first cannulated insertion instrument. The second guide wire can pass through the second cannulated insertion instrument such that the first end and the second end of the second guide wire extend beyond the first end and the second end, respectively, of the second cannulated insertion instrument. The two independent arms can comprise a first arm and a second arm. The first arm can have a proximal end including an intramedullary nail engagement feature therein and a distal end. The second arm can be coupled to the distal end of the first arm and define the first and second apertures. The system can further comprise a fastener that removably couples the first and second arms. The first cannulated insertion instrument and the second cannulated insertion instrument can each include a trocar and at least two soft tissue sleeves.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 1 is a schematic environmental illustration of an exemplary orthopedic fastener system for repairing an anatomy, such as a hip fracture, according to the present teachings;

FIG. 3 is a schematic environmental illustration of a second exemplary first guide instrument for guiding one or more orthopedic fasteners into the anatomy according to the present teachings;

FIG. 3A is a perspective schematic illustration of a driver nose associated with the first guide member of FIG. 3;

FIG. 4 is a top view of a second guide instrument, which can be coupled to the first guide instrument of FIG. 2 for planning a trajectory for the one or more orthopedic fasteners according to the present teachings;

FIG. 5 is a perspective view of the second guide instrument of FIG. 4;

FIG. 6 is a perspective view of the second guide instrument of FIG. 4;

FIG. 11 is a perspective view of the drill bit of FIG. 10;

FIG. 12 is a cross-sectional view of the drill bit of FIG. 9, taken along line 12-12 of FIG. 11;

FIG. 13 is a detail perspective view of a proximal end of the drill bit of FIG. 11;

FIG. 14 is a schematic perspective view of an exemplary drill bit stop coupled to the drill bit of FIG. 11;

FIG. 15 is a perspective view of the drill bit stop of FIG. 14;

FIG. 16 is a cross-sectional view of the exemplary drill bit stop of FIG. 15, taken along line 16-16 of FIG. 15;

FIG. 17 is a perspective view of a trigger associated with the drill bit stop of FIG. 15;

FIG. 23 is a perspective view of a second exemplary orthopedic screw according to the present teachings;

FIG. 24 is an enlarged detail of the second exemplary orthopedic screw of FIG. 23;

FIG. 27 is a perspective view showing the second exemplary orthopedic screw of FIG. 23 with a second driver;

FIG. 28 is an enlarged sectional detail of FIG. 27 showing the engagement of the second exemplary orthopedic screw with the second driver;

FIG. 29 is a enlarged perspective detail of the second driver of FIG. 27;

FIG. 30 is a perspective view showing the second exemplary orthopedic screw of FIG. 23 with a third driver;

FIG. 31 is an enlarged sectional detail of FIG. 30 showing the engagement of the second exemplary orthopedic fastener with the third driver; and FIG. 32 is an enlarged perspective detail of third driver of FIG. 30.

DESCRIPTION OF VARIOUS ASPECTS

Figure 1A:
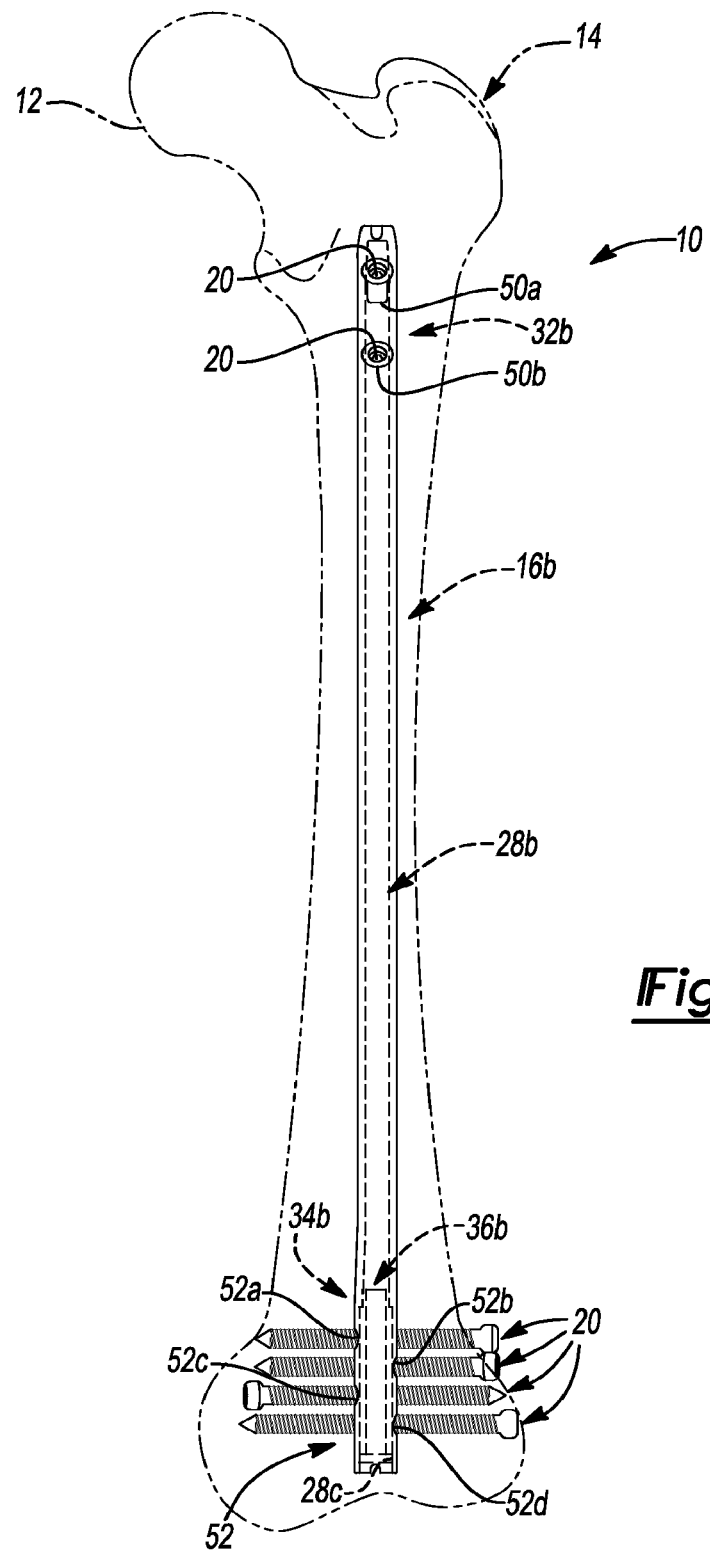
FIG. 1A is a schematic environmental illustration of an exemplary orthopedic fastener system for repairing an anatomy, such as a femoral fracture, according to the present teachings.

The following description is merely exemplary in nature and is not intended to limit the present teachings, application, or uses. It should be understood that throughout the drawings, corresponding reference numerals indicate like or corresponding parts and features. Although the following description is related generally to a system and method for orthopedic fixation for use in an anatomy to repair damaged tissue, such as in a hip fracture, it will be understood that the system and method orthopedic fixation as described and claimed herein, can be used in any appropriate surgical procedure. Further, although the orthopedic fasteners illustrated herein are a type of bone screw, the present teachings can be applied to any type of fastener in which the head of the fastener can be constructed to include several interface features that can be used with various drivers. Further, the present orthopedic fixation teachings are applicable to both primary and reconstruction procedures. Therefore, it will be understood that the following discussions are not intended to limit the scope of the present teachings and claims herein.

Figure 1B:
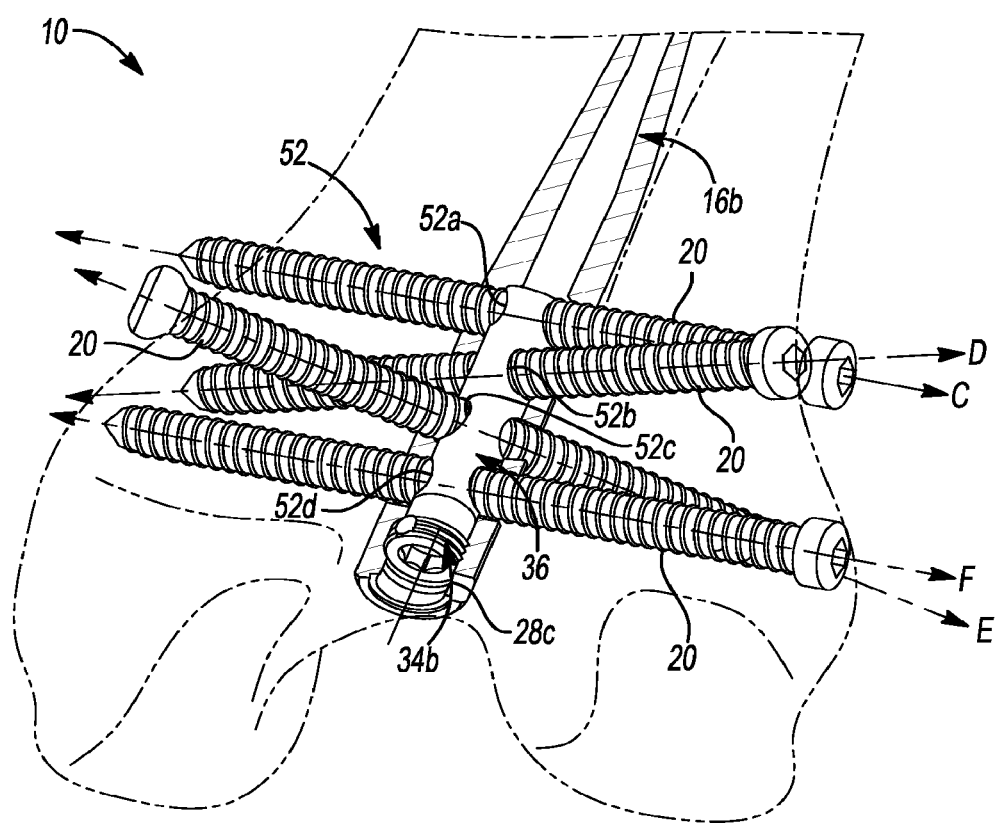
FIG. 1B is a detailed illustration of the orthopedic fastening system of FIG. 1A.

With reference to FIGS. 1 and 1A, an orthopedic fixation system 10 is shown. The orthopedic fixation system 10 can be used to repair damaged tissue in an anatomy, such as a fracture between a femoral head 12 and a femur 14. The orthopedic fixation system 10 can include an intramedullary implant, such as an intramedullary nail 16, one or more reconstructive orthopedic fasteners, such as reconstructive screws 18, and one or more fixation fasteners, such as fixation screws 20. Generally, the intramedullary nail 16 can be inserted into a cavity formed in a medullary canal, and the reconstructive screws 18 can be used to couple the femoral head 12 to the femur via the engagement of the reconstructive screws 18 with the intramedullary nail 16. The fixation screws 20 can secure the intramedullary nail 16 distally to the femur 14, and can provide additional stability.

As will be discussed, various surgical instruments can be employed to couple the orthopedic fixation system 10 to the anatomy. For example, with additional reference to FIGS. 2-10, the surgical instruments can include a first guide instrument 22 (FIG. 2), a second guide instrument 24 (FIGS. 4-6) and a guide wire system 26 (FIGS. 7-9) for use with the first guide instrument 22. A drill system 30 (FIG. 10) can be employed with the guide wire system 26 to prepare the anatomy for receipt of the reconstructive screws 18. Once the anatomy is prepared, the reconstructive screws 18 can be inserted into the anatomy (FIG. 1). It should be noted that although the reconstructive screws 18 are illustrated and described herein as being used in combination with the intramedullary nail 16 to perform a trochanteric femoral fixation, it will be understood that the intramedullary nail 16 as described herein can be used in various surgical procedure, such as a retrograde femoral fixation procedure, and with various combinations of fasteners, and for example, could be used with all fixation screws 20 (FIG. 1A), if desired.

Intramedullary Nail

With reference to FIG. 1, the intramedullary nail 16 can comprise any suitable femoral implant, and generally, can comprise a trochanteric or piriformis fossa entry point antegrade intramedullary nail, or a retrograde intramedullary nail. Suitable trochanteric and piriformis fossa entry point antegrade intramedullary nails and retrograde intramedullary nails are commercially available from Biomet, Inc. of Warsaw, Ind. In addition, the intramedullary nail 16 can comprise one of the exemplary fixation devices described in U.S. patent application Ser. No. 12/183,142, filed on Jul. 31, 2008, and incorporated by reference herein. Thus, the intramedullary nail 16 will not be described in great detail herein. Briefly, however, with reference to FIGS. 1 and 1A, the intramedullary nail 16 can be composed of a suitable biocompatible metal or metal alloy, and could comprise an antegrade intramedullary nail 16a (FIG. 1) or a retrograde intramedullary nail 16b (FIG. 1A).

Antegrade Intramedullary Nail

With reference to FIG. 1, the antegrade intramedullary nail 16a can include a bore 28, which can extend from a proximal end 32 to a distal end 34, and a locking system 36. The bore 28 can facilitate the implantation of the intramedullary nail 16 into the anatomy, and can include internal threads 28a. The internal threads 28a can couple the first guide instrument 22 to the antegrade intramedullary nail 16a, as will be discussed. The proximal end 32 can be angled to facilitate entry of the antegrade intramedullary nail 16a into the anatomy. The proximal end 32 can include one or more discrete throughbores 38 to enable the receipt of one or more fasteners, such as the reconstructive screws 18, therethrough. Typically, the proximal end 32 can include a first throughbore 38a, a second throughbore 38b and a third throughbore 38c, which can be formed at a same starting bore as the first throughbore 38a. Each of the apertures 38 can be formed at an angle to a longitudinal axis of the intramedullary nail 16. The first throughbore 38a and the second throughbore 38b can have an axis A, and the axis A of the first throughbore 38a and the second throughbore 38b can be generally parallel to each other and can intersect the longitudinal axis at about an obtuse angle. The third throughbore 38c can have an axis B, which can intersect each axis A and can intersect the longitudinal axis of the antegrade intramedullary nail 16a at about an acute angle.

The distal end 34 can include one or more discrete throughbores 40. For example, the distal end 34 can include a first throughbore 40a and a second throughbore 40b, each of which can extend substantially transverse to the longitudinal axis of the antegrade intramedullary nail 16a. In one example, the first throughbore 40a can have a circular cross-section, while the second throughbore 40b can have an elliptical cross-section. The throughbores 40 can each receive a suitable fastener, such as a fixation screw 20, and the elliptical cross-section of the second throughbore 40b can enable the fixation screw 20 received therethrough to be angled relative to the longitudinal axis of the antegrade intramedullary nail 16a, if desired.

The locking system 36 of the antegrade intramedullary nail 16a can be received into the bore 28, and generally, can be positioned in the bore 28 at the proximal end 32 of the antegrade intramedullary nail 16a. The locking system 36 can comprise any suitable system capable of securing the reconstructive screws 18 and/or fixation screws 20 to the antegrade intramedullary nail 16a, such as the CORELOCK™ locking system commercially available from Biomet, Inc. of Warsaw, Ind., and described in commonly-owned in U.S. patent application Ser. No. 12/183,142, filed on Jul. 31, 2008, and incorporated by reference herein. Thus, the locking system 36 will not be described in great detail herein. Briefly, however, the locking system 36 can be positioned within the proximal end 32 such that the reconstructive screws 18 and/or fixation screws 20 can pass through the locking system 36 and the throughbores 38 of the antegrade intramedullary nail 16a, so that the locking system 36 can secure the reconstructive screws 18 and/or fixation screws 20 to the antegrade intramedullary nail 16a.

Retrograde Intramedullary Nail

With reference to FIG. 1A, as the retrograde intramedullary nail 16b can have the same or similar features to the antegrade intramedullary nail 16a, the same or similar reference numerals will be used herein to describe the same or similar features. The retrograde intramedullary nail 16b can include a bore 28b, which can extend from a proximal end 32b to a distal end 34b, and the locking system 36. The bore 28b can facilitate the implantation of the retrograde intramedullary nail 16b into the anatomy, and can include internal threads 28c at the distal end 34b. The internal threads 28c can couple the first guide instrument 22 to the retrograde intramedullary nail 16b, as will be discussed.

The proximal end 32b can include one or more discrete throughbores 50 to enable the receipt of one or more fasteners, such as the fixation screws 20, therethrough. Typically, the proximal end 32b can include a first throughbore 50a and a second throughbore 50b, which can each be formed substantially transverse to a longitudinal axis of the retrograde intramedullary nail 16b. In one example, the first throughbore 50a can have an elliptical cross-section, while the second throughbore 50b can have a circular cross-section. The elliptical cross-section of the first throughbore 50a can enable the fixation screw 20 received therethrough to be angled relative to the longitudinal axis of the retrograde intramedullary nail 16b, if desired.

The distal end 34b can be angled to facilitate entry of the retrograde intramedullary nail 16b into the anatomy, if desired. The distal end 34b can include one or more discrete throughbores 52. For example, with reference to FIGS. 1A and 1B, the distal end 34b can include a first throughbore 52a, a second throughbore 52b, a third throughbore 52c and a fourth throughbore 52d. In one example, the first throughbore 52a and the fourth throughbore 52d can each extend substantially transverse to the longitudinal axis of the retrograde intramedullary nail 16b, and the second throughbore 52b and the third throughbore 52c can be substantially oblique to the longitudinal axis.

For example, the first throughbore 52a can have an axis C, the second throughbore 52b can have an axis D, the third throughbore 52c can have an axis E, and the fourth throughbore 52d can have an axis F. In this example, the axis C and the axis F can be generally parallel to each other, while the axis E and the axis D can each be parallel to, but offset from the axis C and the axis F. For example, the axis E and the axis D can each be about 10 to about 30 degrees offset from the C axis.

The throughbores 52 can each receive a suitable fastener, such as the fixation screw 20. In one example, the throughbores 52 can each be spaced a distance apart from each other such that the fixation screws 20 can be inserted without interference from the adjacent fixation screw 20. For example, the first throughbore 52a can be spaced about 33 millimeters (mm) to about 42 mm from an edge 54 of the distal end 34b, while the second throughbore 52b can be spaced about 25 mm to about 35 mm from the edge 54, the third throughbore 52c can be spaced about 17 mm to about 27 mm from the edge 54 and the fourth throughbore 52d can be spaced about 9 mm to about 19 mm from the edge 54.

The locking system 36 of the retrograde intramedullary nail 16b can be received into the bore 28b, and generally, can be positioned in the bore 28b at the distal end 34b of the retrograde intramedullary nail 16b. As the locking system 36 of the retrograde intramedullary nail 16b can comprise any suitable system capable of securing the fixation screws 20 to the retrograde intramedullary nail 16b, such as the CORELOCK™ locking system commercially available from Biomet, Inc. of Warsaw, Ind., and described in commonly-owned in U.S. patent application Ser. No. 12/183,142, filed on Jul. 31, 2008, and incorporated by reference herein, and discussed herein with reference to the antegrade intramedullary nail 16a, the locking system 36 for the retrograde intramedullary nail 16b will not be described further.

First Guide Instrument

Figure 2:
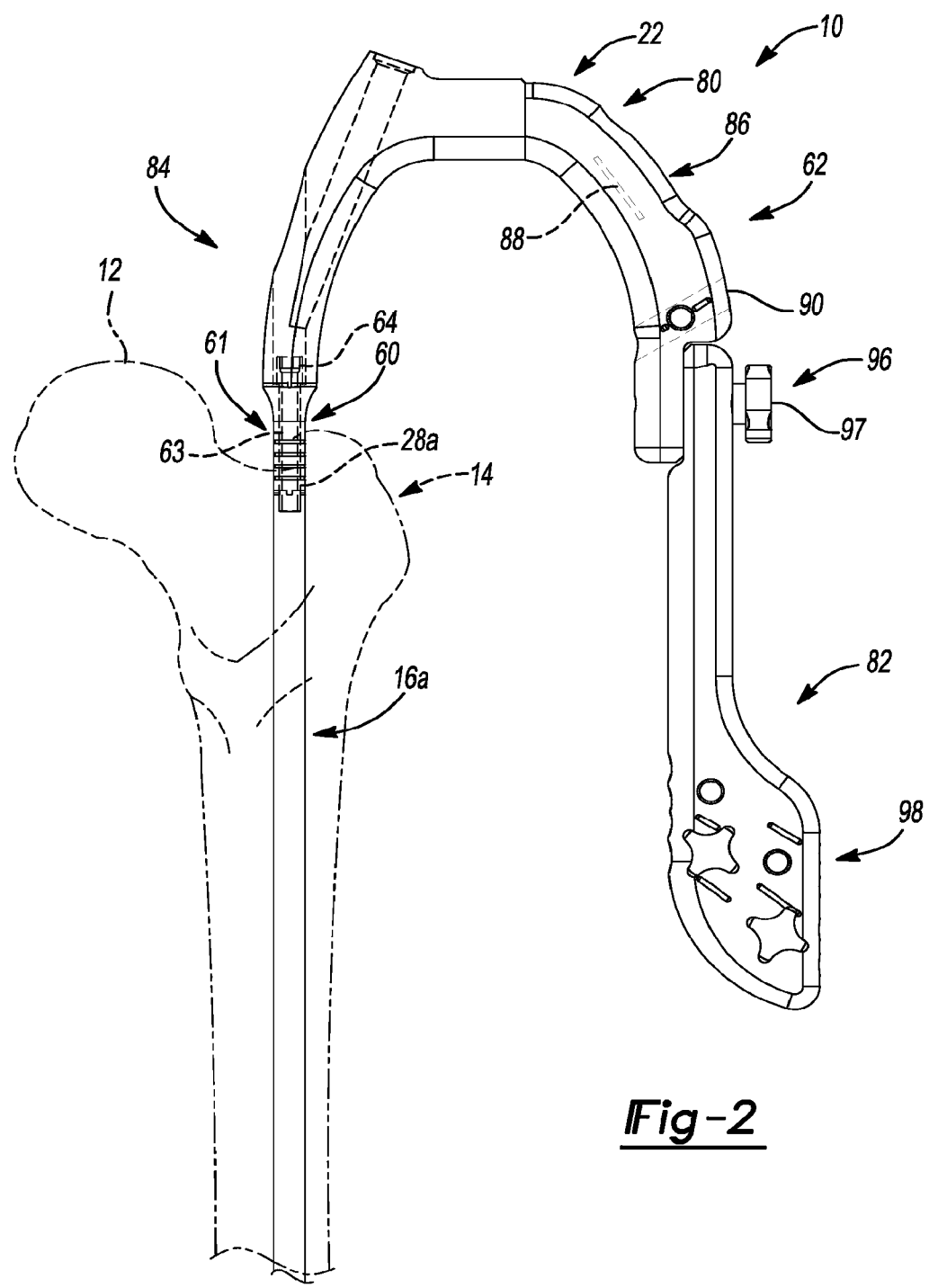
FIG. 2 is a schematic environmental illustration of an exemplary first guide instrument for guiding one or more orthopedic fasteners into the anatomy according to the present teachings.

With reference to FIG. 2, the first guide instrument 22 can be coupled the intramedullary nail 16 to enable a user, such as a surgeon, to guide one or more instruments into the anatomy along a desired path defined by the first guide instrument 22. As the first guide instrument 22 can comprise any suitable targeter or guide that can enable a user to direct one or more instruments into an anatomy along a desired path, the first guide instrument 22 will not be described in great detail herein. Briefly, however, the first guide instrument 22 can include an intramedullary nail engagement feature 60 and a guide 62.

Antegrade Intramedullary Nail

In the example of an antegrade procedure involving an antegrade intramedullary nail 16a, as illustrated in FIG. 2, the intramedullary nail engagement feature 60 can couple the first guide instrument 22 to the antegrade intramedullary nail 16a. Generally, the intramedullary nail engagement feature 60 can include any suitable engagement feature, such as a screw, pin, stake, barb, or other equivalent features to enable the first guide instrument 22 to be coupled to the intramedullary nail 16. For example, the intramedullary nail engagement feature 60 can include a stem 61 and a bolt 63. The stem 61 can define a bore 64, and can include one or more projections 66 formed about an end 68, which can engage one or more notches 70 formed in the intramedullary nail 16 to ensure the first guide instrument 22 is properly coupled to the intramedullary nail 16. The bore 64 can enable the bolt 63 to pass through the stem 61. The bolt 63, once inserted into the stem 61, can engage the threads 28a formed in the antegrade intramedullary nail 16a to couple the first guide instrument 22 to the antegrade intramedullary nail 16a.

With continued reference to FIG. 2, the guide 62 can include a first arm member 80 and a second arm member 82. The first arm member 80 can include a proximal end 84, a distal end 86 and one or more radio-opaque markers 88. In one example, the first arm member 80 can be coupled to the intramedullary nail engagement feature 60 at the proximal end 84, and can be coupled to the second arm member 82 at the distal end 86. Thus, in the case of an antegrade intramedullary nail 16a, the guide 62 can be substantially L-shaped.

The distal end 86 of the first arm member 80 can include one or more apertures 90. The apertures 90 can enable the guide wire system 26 to be coupled to, and guided by, the first guide instrument 22. Generally, in the case of an antegrade intramedullary nail 16a, for example, the distal end 86 of the first arm member 80 can include a single aperture 90, which can enable the guide wire system 26 to guide a fixation screw 20 into the third throughbore 40c of the antegrade intramedullary nail 16a in an interlock procedure (not specifically shown).

Figure 2A:
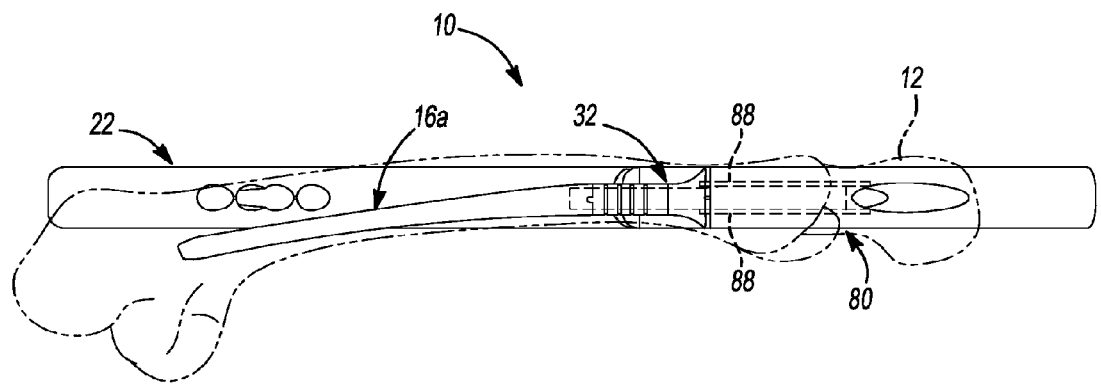
FIG. 2A is a schematic environmental illustration of an exemplary image acquired that includes the first guide of FIG. 2.

The radio-opaque markers 88 can be disposed within the first arm member 80. For example, with reference to FIG. 2A, two radio-opaque markers 88 can be disposed within the first arm member 80 and can be generally parallel to, but spaced apart from each other in the same plane such that a lateral image acquired by a suitable imaging source, such as a C-arm fluoroscope, can illustrate the location of the two radio-opaque markers 88. Generally, the radio-opaque markers 88 can be positioned such that when the first guide instrument 22 is coupled to the intramedullary nail 16, the radio-opaque markers 88 provide guide lines for the surgeon to ensure that the proximal end 32 of the intramedullary nail 16 is properly located within the anatomy. Thus, as shown in FIG. 2A, in a lateral image of an antegrade intramedullary nail 16a, the radio-opaque markers 88 can define a range or boundary for the position of the proximal end 32 of the antegrade intramedullary nail 16a within the anatomy.

Figure 2B:
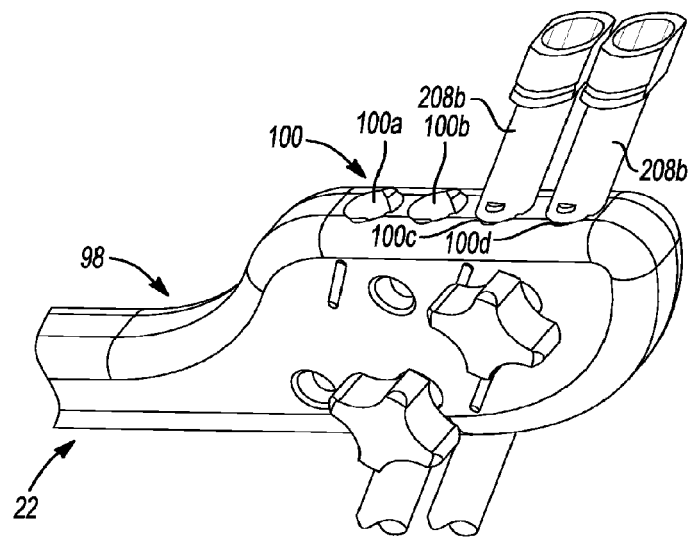
FIG. 2B is a schematic detail illustration of the first guide instrument of FIG. 2.

With reference back to FIG. 2, the second arm member 82 of the guide 62 can include a proximal end 96 and a distal end 98. The proximal end 96 of the second arm member 62 can be coupled to the distal end 86 of the first arm member 80, such as through a fastener 97, and the distal end 98 can include one or more apertures 100, as best shown in FIG. 2B. The apertures 100 can enable the guide wire system 26 to be coupled to, and guided by, the first guide instrument 22. Generally, in the case of an antegrade intramedullary nail 16a, for example, the distal end 98 of the second arm member 82 can include four apertures 100, which can enable the guide wire system 26 to guide multiple reconstructive screws 18 into the anatomy. For example, a first aperture 100a and a second aperture 100b can be angled to guide a first and a second reconstructive screw 18a into the anatomy during a trochanteric procedure involving an appropriate antegrade intramedullary nail 16a. A third aperture 100c and a fourth aperture 100d can be angled to guide a first and a second reconstructive screw 18a into the anatomy during a piriformis fossa procedure involving an appropriate antegrade intramedullary nail 16a.

Retrograde Intramedullary Nail

With reference to FIG. 3, in the case of a retrograde intramedullary nail 16b, the guide 22 can include an intramedullary nail engagement feature 60b, which can couple the first guide instrument 22 to the retrograde intramedullary nail 16b. The intramedullary nail engagement feature 60b can include any suitable engagement feature, such as a screw, pin, stake, barb, or other equivalent features to enable the first guide instrument 22 to be coupled to the retrograde intramedullary nail 16b. For example, in the case of a retrograde intramedullary nail 16b, the intramedullary nail engagement feature 60b can include a driver nose 72 and a bolt 74, as shown in FIG. 3A. The driver nose 72 can define a bore 75 (FIG. 3A), a throughbore 77, and can include one or more projections 76 formed about an end 78, which can engage one or more notches 79 formed in the intramedullary nail 16b to ensure the first guide instrument 22 is properly coupled to the intramedullary nail 16. The bore 75 can enable the bolt 74 to pass through the driver nose 72. The bolt 74, once inserted into the driver nose 72, can engage the threads 28c formed in the retrograde intramedullary nail 16b to couple the first guide instrument 22 to the retrograde intramedullary nail 16b.

With reference to FIG. 3, the guide 62b associated with a retrograde intramedullary nail 16b can include a first arm member 80b and a second arm member 82b. The first arm member 80b can include a proximal end 84b and a distal end 86b. In one example, the first arm member 80b can be coupled to the intramedullary nail engagement feature 60 at the proximal end 84b, and can be coupled to or integrally formed with the second arm member 82b at the proximal end 84b. Thus, in the case of a retrograde intramedullary nail 16b, the guide 62 can be substantially U-shaped and can be formed into one-piece.

Figure 3B:
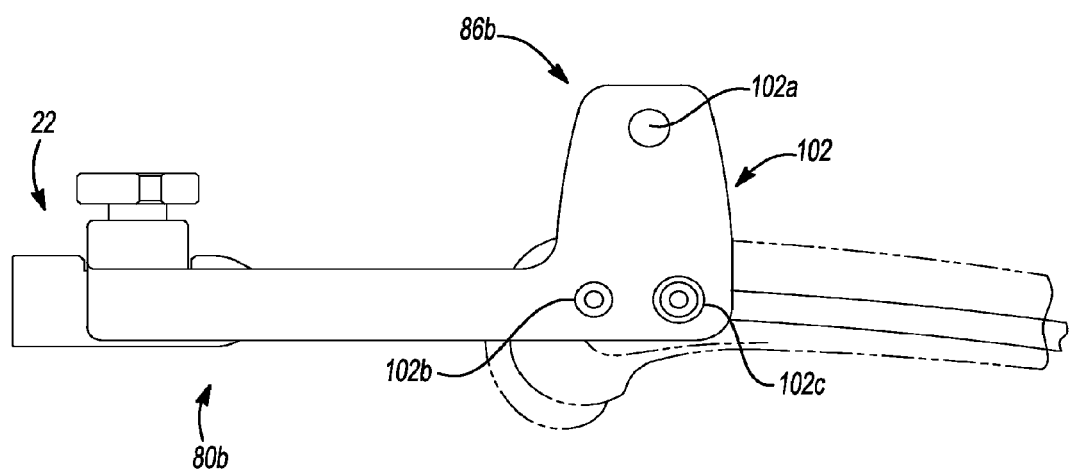
FIG. 3B is a side view of the first guide instrument of FIG. 3.

With reference to FIG. 3B, the distal end 86b of the first arm member 80b can include one or more apertures 102. The apertures 102 can enable the guide wire system 26 to be coupled to, and guided by, the first guide instrument 22. Generally, in one example, as illustrated in FIG. 3B, the distal end 86b of the first arm member 80b can include three apertures 102, a first aperture 102a, a second aperture 102b and a third aperture 102c. The first aperture 102a can be configured to direct the guide wire system 26 to position a fastener, such as a fixation screw 20, in an oblique location in the anatomy. The first aperture 102a can be positioned above the second aperture 102b and the third aperture 102c, and can be angled towards the second aperture 102b and the third aperture 102c to facilitate the placement of the fixation screw 20 at an oblique angle. The second aperture 102b and the third aperture 102c can generally be positioned adjacent to each other and transverse to the anatomy, to direct the guide wire system 26 to position a fastener, such as a fixation screw 20, in a location transverse to the longitudinal axis of the retrograde intramedullary nail 16b.

The second arm member 82b of the guide 62 can include a proximal end 96b and a distal end 98b. The proximal end 96b of the second arm member 62 can be coupled to the distal end 86b of the first arm member 80b, and the distal end 98b can include the one or more apertures 102 associated with the distal end 86b of the first arm member 80b. As the apertures 102 of the distal end 98b of the second arm member 82b can be substantially similar to the apertures 102 of the distal end 86b of the first arm member 80b, the distal end 98b will not be discussed further herein.

Thus, in both an antegrade and a retrograde procedure, the guide 62 of the first guide instrument 22 can serve to direct a user, such as a surgeon, in the placement of the reconstructive screws 18 and/or fixation screws 20 relative to the anatomy, via the guide wire system 26.

Second Guide Instrument

With reference to FIGS. 4-6, the second guide instrument 24 can be selectively coupled to the first guide instrument 22. Generally, the second guide instrument 24 can be used to ensure that the antegrade intramedullary nail 16a and first guide instrument 22 are properly aligned during an antegrade procedure. It should be understood, however, that the second guide instrument 24 as described and illustrated herein may be applicable to various other surgical procedures, and thus, may not be limited to an antegrade procedure. Typically, the second guide instrument 24 can include a body 110 and a post 112.

As best shown in FIGS. 5 and 6, when used with an antegrade procedure, the body 110 can be generally D-shaped, and can define an opening 114, a bore 116 substantially opposite the opening 114, one or more gripping members 118 and a slot 120. The opening 114 can enable the second guide instrument 24 to be positioned onto the first guide instrument 22, and thus, the opening 114 can be about equal to a width of the first guide instrument 22. The opening 114 can be defined by ends 122 of the body 110. The post 112 can be coupled to the bore 116 and the post 112 can pass through the bore 116 and into one of the apertures 90 of the first guide instrument 22 to secure and align the second guide instrument 24 with the first guide instrument 22. Generally, the second guide instrument 24 can be aligned with the aperture 90 associated with the desired reconstructive procedure, such as a trochanteric or piriformis fossa procedure.

The gripping members 118 can be coupled to or formed on the ends 122 of the body 110, and can generally engage the first guide instrument 22 when the second guide instrument 24 is coupled to the first guide instrument 22 to further secure the second guide instrument 24 to the first guide instrument 22. In one example, the gripping members 118 can be projections that extend from the ends 122, but the gripping members 118 could also comprise bearings, notches, ball plungers, etc. formed of any suitable metal, metal alloy or polymeric material suitable to grip the surface of the first guide instrument 22.

With reference to FIGS. 4-5, the slot 120 can generally be formed on a top surface 124 of the body 110. The slot 120 can have a width sized to receive one or more guide wires, such as the guide wires 202, 204 discussed with regard to the guide wire system 26, which can serve as radio-opaque markers during an image acquired by a suitable imaging device, such as a fluoroscopic C-arm. The slot 120 can generally be formed on the top surface 124 so that when the guide wires 202, 204 are received into the slot 120, the guide wires 202, 204 can be aligned with a trajectory of the guide wire system 26 through the respective aperture 90 on the first guide instrument 22. Thus, when an image is taken of the second guide instrument 24, the guide wires 202, 204 can illustrate the trajectory through the respective aperture 90 associated with the first guide instrument 22.

In one example, two guide wires 202, 204 can be received into the slot 120. Then, an image can be obtained using the imaging device. The image can illustrate the positioning of the guide wire system 26 into the femur 14 and femoral head 12. In addition, if only one guide wire 202, 204 appears in the image, then the surgeon can ensure that he has obtained a substantially true anterior-posterior image.

The post 112 can be received through the bore 116 and into the respective aperture 90 to couple the second guide instrument 24 to the first guide instrument 22. The post 112 can have a length sized such that the post 112 can terminate substantially adjacent to a side S of the first guide instrument 22, as best shown in FIG. 4. Typically, the post 112 does not serve as a radio-opaque marker for identifying a trajectory through the first guide instrument 22 as the post 112 does not extend sufficiently towards the anatomy.

Thus, the second guide instrument 24 in combination with one or more guide wires 202, 204 can be used to verify the proposed trajectory of the guide wire system 26 based on the current alignment of the first guide instrument 22, which can ensure that any fasteners guided by the guide wire system 26 may be inserted into the desired aperture 38 in the antegrade intramedullary nail 16a.

Guide Wire System

Figure 7:
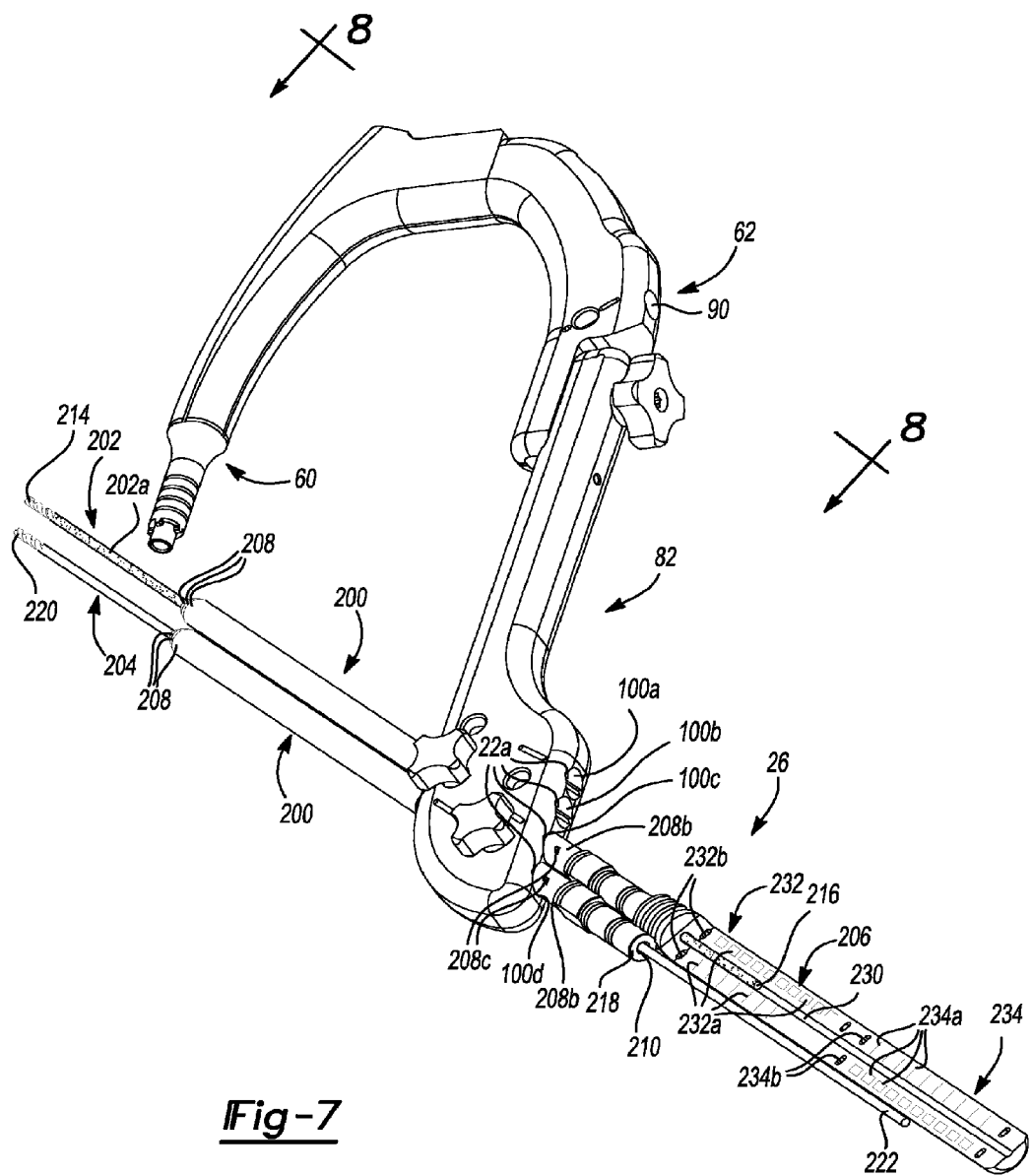
FIG. 7 is a perspective view of the first guide instrument including dual reconstructive wires according to the present teachings.
Figure 8:
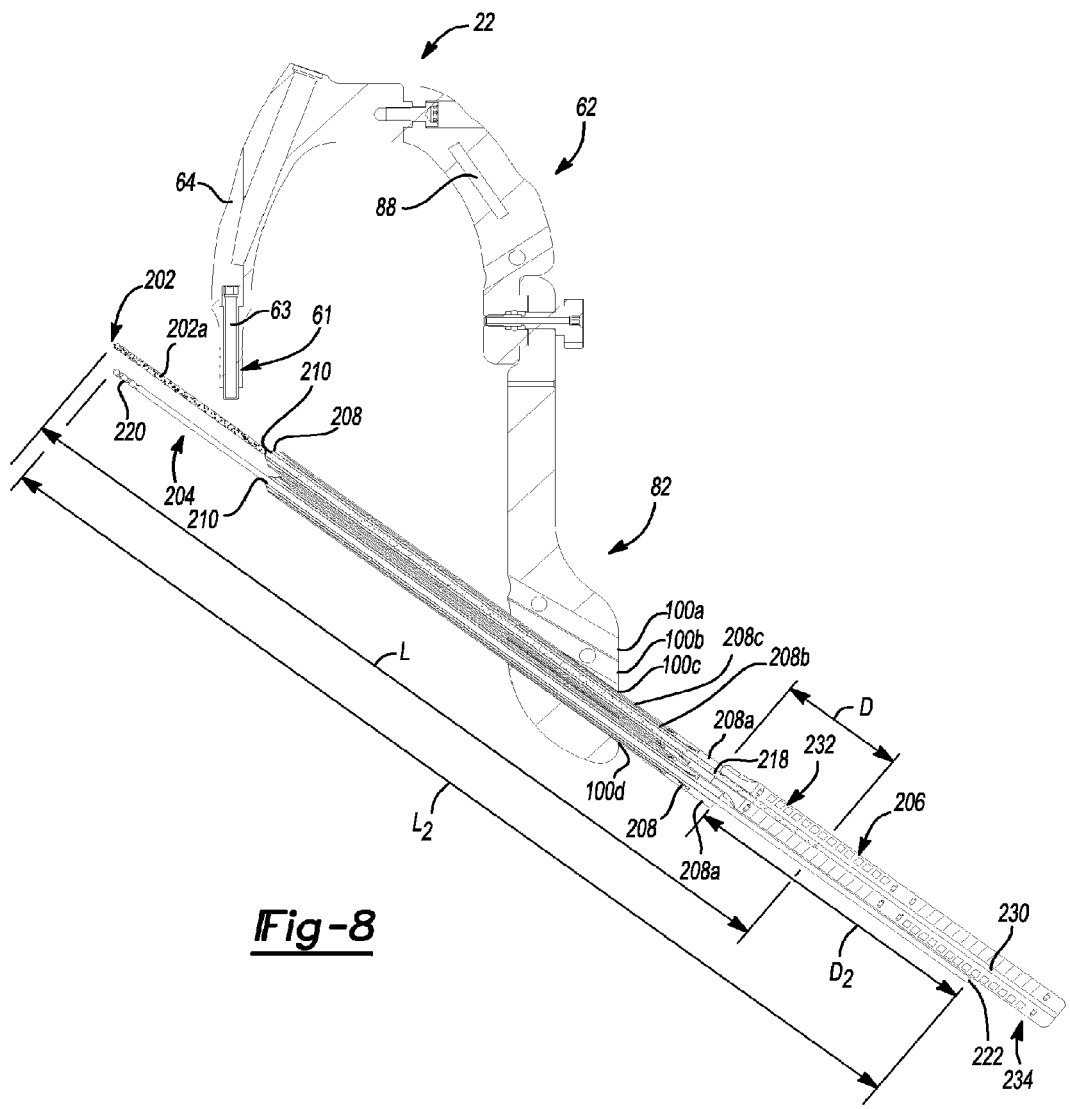
FIG. 8 is a cross-sectional view of the first guide instrument including the dual reconstructive wires taken along line 8-8 of FIG. 7.
Figure 9:
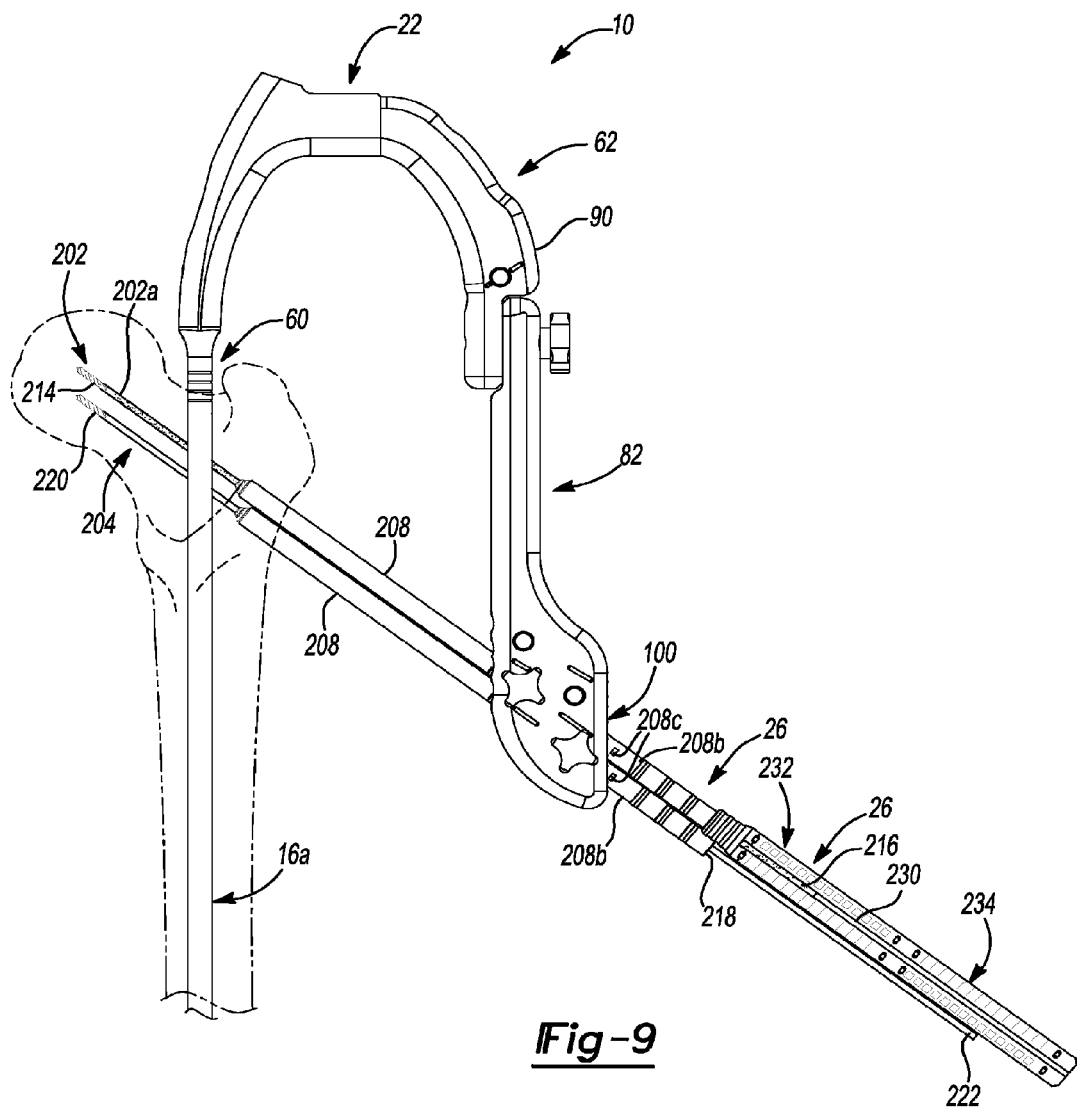
FIG. 9 is an schematic environmental illustration of the first guide instrument including the dual reconstructive wires of FIG. 7 shown with the dual reconstructive wires inserted in an anatomy.

In one example, with reference to FIGS. 7-9, in the case of an antegrade intramedullary nail 16a (FIG. 9), the guide wire system 26 can include one or more cannulated insertion instruments 200, a first reconstructive guide wire 202, a second reconstructive guide wire 204 and a measuring gage 206. Although the guide wire system 26 is discussed and illustrated herein as being used with an antegrade intramedullary nail 16a, it will be understood that the guide wire system 26 can be used with a retrograde intramedullary nail 16b with substantially little or no modification, and thus, the discussion and illustration of the guide wire system 26 is not intended to limit the guide wire system 26 to only an antegrade surgical procedure.

The cannulated insertion instrument 200 can be received into the apertures 100 to guide the first reconstructive wire 202 and the second reconstructive wire 204 into the anatomy. As the cannulated insertion instrument 200 can comprise any instrument suitable for guiding the first reconstructive wire 202 and the second reconstructive wire 204 into the anatomy until the first reconstructive wire 202 and the second reconstructive wire 204 are adjacent to a bone in the anatomy, such as a femur, the cannulated insertion instrument 200 will not be discussed in great detail herein. Briefly, however, with reference to FIG. 2, the cannulated insertion instrument 200 can include one or more soft tissue sleeves 208 and a trocar (not specifically shown). It should be noted that although two cannulated insertion instruments 200 are illustrated herein, any number of cannulated insertion instruments 200 could be employed, and further, the same reference numerals will be used to denote the same or similar features of the illustrated cannulated insertion instruments 200. Generally, with reference to FIGS. 7 and 8, the cannulated insertion instrument 200 can include three soft tissue sleeves 208, however, any suitable number of soft tissue sleeves 208 could be employed. The soft tissue sleeves 208 can each define a throughbore 210, and a diameter of each of the soft tissue sleeves 208 can increase relative to each other soft tissue sleeve 208 such that the soft tissue sleeves 208 can be nested within each other.

In this regard, the soft tissue sleeves 208 can be assembled one inside of the other and the trocar can be inserted within an innermost soft tissue sleeve 208a. The assembly of the soft tissue sleeves 208 with the trocar can form a generally conical shape, which can facilitate insertion of the cannulated insertion instrument 200 into the anatomy. In addition, the outer soft tissue sleeve 208b can include a stop 208c, which can abut the first guide instrument 22, and for example, can engage a notch 22a formed at adjacent to the apertures 100 of the second arm member 82. The stop 208c can thereby provide a depth stop for the insertion of the soft tissue sleeves 208 into the anatomy, and can also be used by the surgeon in the planning of the respective surgical procedure.

Once the soft tissue sleeves 208 are inserted to a desired depth in the anatomy, such as adjacent to a desired bone in the anatomy, the trocar can be removed and the throughbore 210 of the innermost soft tissue sleeve 208a can be used to guide one or more instruments to the bone in the anatomy, such as the first reconstructive wire 202 and the second reconstructive wire 204. In addition, the known length of the soft tissue sleeves 208 can enable the user, such as the surgeon, to measure a depth of the first reconstructive wire 202 and the second reconstructive wire 204 within the anatomy, as will be discussed.

With reference to FIGS. 7 and 8, the first reconstructive wire 202 can be configured to guide an instrument and/or an implant into the anatomy, such as a drill and/or an orthopedic screw. The first reconstructive wire 202 can be comprised of any suitable biocompatible material, such as a metal, metal alloy or polymer, and can include the colored coating 202a, such as a titanium nitride coating, to enable the user to visually distinguish between the first reconstructive wire 202 and the second reconstructive wire 204. The first reconstructive wire 202 can include a first end 214 and a second end 216. The first end 214 can include a bone engagement feature, such as a plurality of threads, a taper, stake, barbs or other equivalent feature to couple the first reconstructive wire 202 to the anatomy. With reference to FIG. 8, the second end 216 can extend a distance D beyond an end 218 of the outermost soft tissue sleeve 208b to enable the user, such as the surgeon, to guide one or more instruments or implants into the anatomy.

Further, the first reconstructive wire 202 can have a length L that is selected to enable the first reconstructive wire 202 to extend through the soft tissue sleeves 208 such that the first end 214 can engage the bone in the anatomy FIG. 8. Generally, with reference to FIG. 8, the length L of the first reconstructive wire 202 can enable the second end 216 of the first reconstructive wire 202 to extend the distance D from the end 218 of the outermost soft tissue sleeve 208b. For example, the length L of the first reconstructive wire 202 can range from about 400 millimeters to about 500 millimeters, and generally, can range from about 430 millimeters to about 490 millimeters. As a length of the outermost soft tissue sleeve 208b is known, and the length L of the first reconstructive wire 202 is known, by measuring the distance D of the first reconstructive wire 202 that extends from the end 218 of the outermost soft tissue sleeve 208b, the user can determine the depth of the first reconstructive wire 202 within the anatomy.

With reference to FIGS. 7-9, the second reconstructive wire 204 can be configured to guide an instrument and/or an implant into the anatomy, such as a drill and/or an orthopedic screw. The second reconstructive wire 204 can be comprised of any suitable biocompatible material, such as a metal, metal alloy or polymer, and can comprise a polished metal finish, to enable the user to visually distinguish between the second reconstructive wire 204 and the first reconstructive wire 202. The second reconstructive wire 204 can include a first end 220 and a second end 222. The first end 220 can include a bone engagement feature, such as a plurality of threads, a taper, stake, barbs or other equivalent feature to couple the second reconstructive wire 204 to the anatomy. The second end 222 can extend a distance D2 beyond the end 218 of the outermost soft tissue sleeve 208b to enable the user, such as the surgeon, to guide one or more instruments or implants into the anatomy, such as the reconstructive screws 18.

In addition, the second reconstructive wire 204 can have a length L2 that is selected to enable the second reconstructive wire 204 to extend through the soft tissue sleeves 208 such that the first end 220 of the second reconstructive wire 204 can engage the bone in the anatomy. Generally, the length L2 of the second reconstructive wire 204 can enable the second end 222 of the second reconstructive wire 204 to extend the distance D2 from the end 218 of the outermost soft tissue sleeve 208b. For example, the length L2 of the second reconstructive wire 204 can range from about 430 millimeters to about 550 millimeters, and generally, can range from about 495 millimeters to about 555 millimeters. As the length of the outermost soft tissue sleeve 208b is known, and the length L2 of the second reconstructive wire 204 is known, by measuring the distance D2 of the second reconstructive wire 204 that extends from the end 218 of the outermost soft tissue sleeve 208b, the user can determine the depth of the second reconstructive wire 204 within the anatomy.

Typically, the second reconstructive wire 204 can have a longer length L2 than the length L of the first reconstructive wire 202 such that the second reconstructive wire 204 can be inserted into the anatomy after the insertion of the first reconstructive wire 202 to prevent instruments associated with the placement of the second reconstructive wire 204 from contacting the first reconstructive wire 202, as will be discussed below. Generally, the difference between the lengths L and L2 of the first reconstructive wire 202 and the second reconstructive wire 204 can range from about 30 millimeters to about 150 millimeters, and typically between about 30 millimeters and about 100 millimeters.

With reference to FIG. 8, the measuring gage 206 can enable the user to measure the distance D of the first reconstructive wire 202 and the distance D2 of the second reconstructive wire 204 that extends beyond the end 218 of the outermost soft tissue sleeve 208b. This can enable the user, such as the surgeon, to determine the depth of the respective first reconstructive wire 202 and the second reconstructive wire 204 within the anatomy. The measuring gage 206 can include a bore 230, a first reconstructive wire calibration scale 232 and a second reconstructive wire calibration scale 234.

As best illustrated in FIG. 7, the bore 230 can enable the user to slide the measuring gage 206 onto the second end 216 or second end 222 of the respective first reconstructive wire 202 or the second reconstructive wire 204. The first reconstructive wire calibration scale 232 can include one or more calibration markings 232a and a key 232b. The calibration markings 232a can enable the user to determine the depth of the first reconstructive wire 202 within the anatomy when the measuring gage 206 is inserted over the second end 216 of the first reconstructive wire 202 and adjacent to the end 218 of the outermost soft tissue sleeve 208b. Thus, the calibration markings 232a can convert the distance D of the second end 216 into a measurement that corresponds to the depth of the first reconstructive wire 202 within the anatomy. The key 232b can comprise at least one color-coded area that can correspond with the colored coating of the first reconstructive wire 202, such as gold, to enable the user to visually verify that the first reconstructive wire 202 is properly aligned within the measuring gage 206. By measuring the depth of the first reconstructive wire 202 with the measuring gage 206, the user can verify that the first reconstructive wire 202 is properly positioned within the anatomy.

The second reconstructive wire calibration scale 234 can include one or more calibration markings 234a and a key 234b. The calibration markings 234a can enable the user to determine the depth of the second reconstructive wire 204 within the anatomy when the measuring gage 206 is inserted over the second end 222 of the second reconstructive wire 204 and adjacent to the end 218 of the outermost soft tissue sleeve 208b. Thus, the calibration markings 234a can convert the distance D2 of the second end 222 into a measurement that corresponds to the depth of the second reconstructive wire 204 within the anatomy. The key 234b can comprise at least one color coded area that can correspond with the color of the second reconstructive wire 204, such as gray or silver, to enable the user to visually verify that the second reconstructive wire 204 is properly aligned within the measuring gage 206. By measuring the depth of the second reconstructive wire 204 with the measuring gage 206, the user can verify that the second reconstructive wire 204 is properly positioned within the anatomy.

With reference to FIG. 9, the guide wire system 26 can be used to guide one or more instruments into an anatomy, such as the femur 14, which includes the femoral head 12. In order to couple the guide wire system 26 to femur 14 and femoral head 12, the first guide instrument 22 can be coupled to the antegrade intramedullary nail 16a disposed in the femur 14. In this regard, the intramedullary nail engagement feature 60 of the first guide instrument 22 can be coupled to the antegrade intramedullary nail 16a such that the apertures 90 of the guide 62 can be properly aligned to enable the insertion of the first reconstructive wire 202 and the second reconstructive wire 204 into a desired position.

With the first guide instrument 22 coupled to the antegrade intramedullary nail 16a, the soft tissue sleeves 208 can be assembled within each other, and the trocar can be inserted into the innermost soft tissue sleeve 208a. The assembled soft tissue sleeves 208 and trocar can then be inserted into the anatomy until the cannulated insertion instrument 200 reaches the femur 14 and femoral head 12. This process can be repeated as necessary to provide passageways for a desired number of reconstructive wires within the anatomy, and thus, the illustration of two cannulated insertion instruments 200 is merely exemplary, as any number of cannulated insertion instruments 200 could be inserted into the anatomy.

Once the cannulated insertion instruments 200 contact the femur 14 and femoral head 12, the trocar can be removed from the soft tissue sleeves 208, and the first reconstructive wire 202 can be inserted into the anatomy. The first reconstructive wire 202 can be driven through the throughbore 210 of the innermost soft tissue sleeve 208a. The first reconstructive wire 202 can be driven into the anatomy via any suitable instrument, such as through a powered instrument (e.g., a drill) or a manually powered instrument (e.g., manual manipulation of the second end 216 of the first reconstructive wire 202). Once the first reconstructive wire 202 is coupled to the anatomy, the second reconstructive wire 204 can be coupled to the anatomy.

Due to the length L of the first reconstructive wire 202 (FIG. 8), the second reconstructive wire 204 can be coupled to the anatomy without contacting the first reconstructive wire 202. In this regard, the instrument used to drive the second reconstructive wire 204 cannot contact the first reconstructive wire 202 as the second end 222 of the second reconstructive wire 204 extends at least a distance D3 beyond the second end 216 of the first reconstructive wire 202. With reference to FIG. 9, in order to drive the second reconstructive wire 204 into the anatomy, the second reconstructive wire 204 can be driven through the throughbore 210 of the innermost soft tissue sleeve 208a. The second reconstructive wire 204 can be driven into the anatomy via any suitable instrument, such as through a powered instrument (e.g., a drill) or a manually powered instrument (e.g., manual manipulation of the second end 222 of the second reconstructive wire 204).

With the first reconstructive wire 202 and the second reconstructive wire 204 coupled to the anatomy, the measuring gage 206 can be used to verify that the first reconstructive wire 202 and the second reconstructive wire 204 are at a desired depth in the anatomy. The user can slide the measuring gage 206 over the second end 216 of the first reconstructive wire 202 and can use the first reconstructive wire calibration scale 232 to measure the distance D that the first reconstructive wire 202 extends beyond the outermost soft tissue sleeve 208b, which can correspond to the depth of the first reconstructive wire 202 within the anatomy, as shown in FIGS. 7-9. Then, the user can slide the measuring gage 206 over the second end 222 of the second reconstructive wire 204 and can use the second reconstructive wire calibration scale 234 to measure the distance D2 that the second reconstructive wire 204 extends beyond the outermost soft tissue sleeve 208b, which can correspond to the depth of the second reconstructive wire 204 within the anatomy. If the first reconstructive wire 202 and the second reconstructive wire 204 are properly positioned within the anatomy, then the user can use the first reconstructive wire 202 and the second reconstructive wire 204 to guide one or more instruments into the anatomy, such as the drill system 30 and/or the reconstructive screws 18.

Drill System

Figure 10:
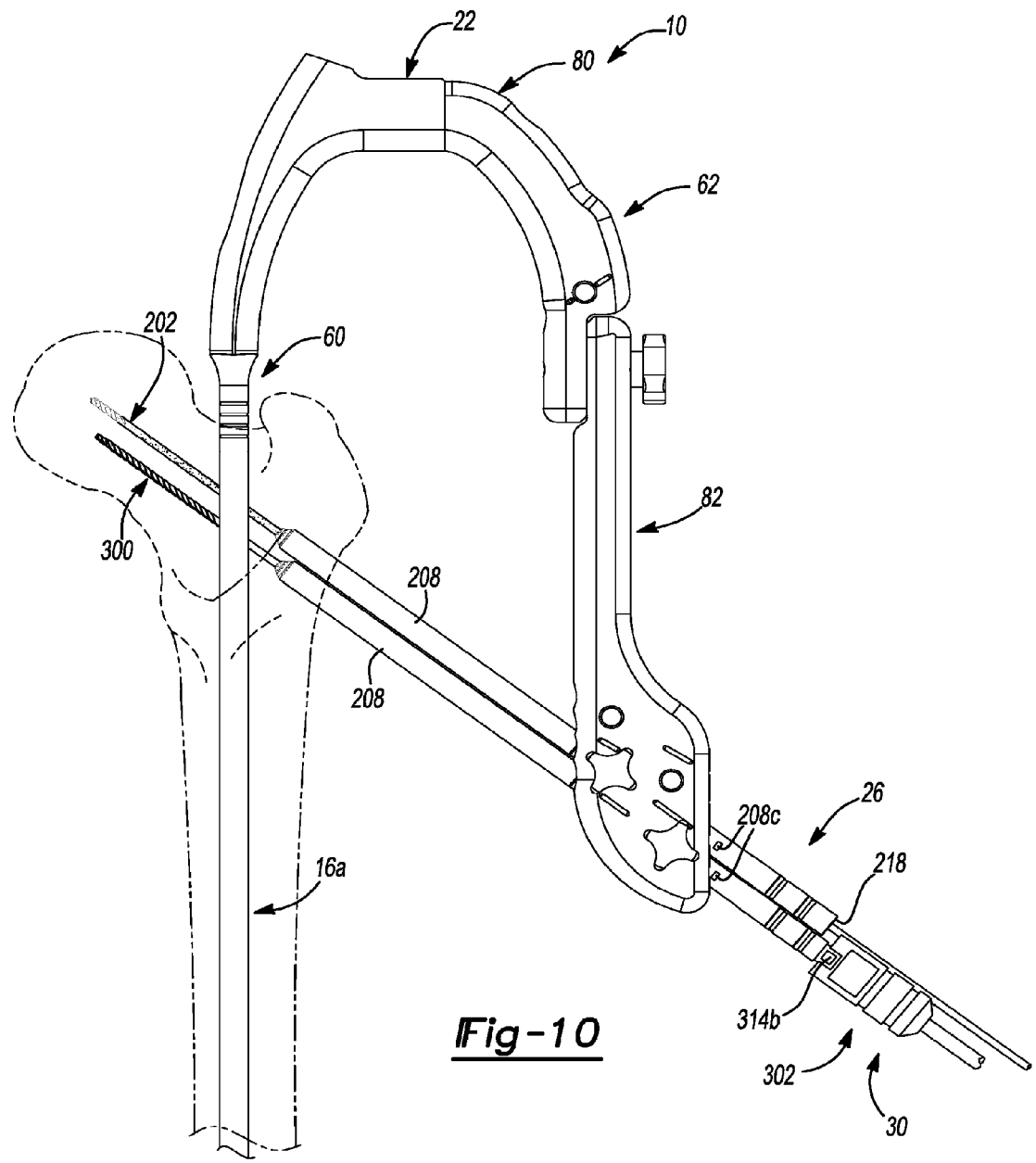
FIG. 10 is a schematic environmental illustration of the first guide instrument in which a drill bit according to the present teachings is received within one of the cannulated insertion instruments.

With reference to FIG. 10, the drill system 30 can be employed with the guide wire system 26 to prepare the anatomy for receipt of the reconstructive screws 18. It should be understood that although the drill system 30 is described and illustrated herein as being used in an antegrade procedure involving the antegrade intramedullary nail 16a, the drill system 30 can be used in any suitable surgical procedure, such as in a retrograde surgical procedure. Generally, the drill system 30 can configured to pass over the first reconstructive wire 202 and the second reconstructive wire 204 so that the guide wire system 26 can guide the drill system 30 into the desired position in the anatomy. The drill system 30 can generally include a drill bit 300 and a drill stop 302. The drill bit 300 can be used to form a bore in the anatomy that has a depth or length set by the manipulation of the drill stop 302.

With reference to FIGS. 11-13, the drill bit 300 can be formed of any suitable metal, metal alloy or composite material, and can be cannulated so that the drill bit 300 can be passed over and directed by the guide wire 202, 204 into the anatomy (FIGS. 10 and 12). The drill bit 300 can include a proximal end 304, an intermediate portion 306 and a distal end 308. With reference to FIGS. 12 and 13, the proximal end 304 can be configured to cut through the anatomy, and can include one or more cutting sections 310 through which one or more cutting flutes 312 pass to comprise a cutting surface for the drill bit 300.

The cutting sections 310 can include about four cutting sections, a first cutting section 310a, a second cutting section 310b, a third cutting section 310c and a fourth cutting section 310d, however, any number of cutting sections 310 could be employed, from about one cutting section 310 to about ten cutting sections 310, for example. The cutting sections 310a-d can be configured to provide a lead-in for the drill bit 300 into the anatomy. In this regard, the cutting sections 310 can each increase in diameter from the first cutting section 310a to the fourth cutting section 310d to facilitate the engagement and advancement of the drill bit 300 into the anatomy. In one example, an angle from about thirty to about sixty degrees can be provided between each of the cutting sections 310 to transition between the cutting sections 310. In addition, with reference to FIG. 13, the cutting sections 310 can generally increase in diameter from about 0.01 millimeters (mm) to about 0.03 mm starting from the first cutting section 310a. Thus, the second cutting section 310b can have a diameter $d_b$ about 0.01 mm to about 0.03 mm greater than a diameter $d_a$ of the first cutting section 310a, the third cutting section 310c can have a diameter $d_c$ about 0.01 mm to about 0.03 mm greater than the diameter $d_b$ of the second cutting section 310*b* and the fourth cutting section 310*d* can have a diameter $d_d$ about 0.01 mm to about 0.03 mm greater than the diameter $d_c$ of the third cutting section 310*c*.

Generally, as shown in FIG. 12, the drill bit 300 can include about four cutting flutes 312, however, it will be understood that the drill bit 300 can include any desirable number of cutting flutes 312, from about two to about eight, for example. The cutting flutes 312 can wind about the proximal end 304 of the drill bit 300 and can form a continuous cutting surface that transitions in diameter along the cutting sections 310, as shown in FIG. 13. In one example, if four cutting flutes 312 are formed on the drill bit 300, each cutting flute 312 can be about evenly spaced apart from each other, and can each be formed to have an about 20 degrees to about 40 degrees right hand spiral.

With reference to FIG. 11, the intermediate portion 306 can couple the proximal end 304 to the distal end 308 and can include one or more depth markers 314. The depth markers 314 can be formed about the diameter of the intermediate portion 306, and can each be spaced by a groove 314*a*. The depth markers 314 can include a depth label 314*b*. The depth label 314*b* can indicate a depth of the drill bit 300 in the anatomy, and thus, the depth markers 314 can cooperate with the drill stop 302 to enable the section of a desired depth for the drill bit 300 to traverse within the anatomy, as will be discussed further herein. Generally, the depth markers 314 can indicate the depth in millimeters, however, the depth markers 314 could correspond to any desired measurement scale.

The distal end 308 can be configured to enable the drill bit 300 to be coupled to a suitable drill. As the drill bit 300 can be coupled to any suitable drill, via the distal end 308, the distal end 308 will not be described in great detail herein. Briefly, however, note that the distal end 308 can include at least one groove 308*a*. The at least one groove 308*a* can enable a chuck of the drill to engage the drill bit 300, as is generally known.

With reference to FIGS. 10 and 14-17, as discussed, the drill stop 302 can cooperate with the drill bit 300 to enable the surgeon to select a desired depth for the drill bit 300 to traverse in the anatomy (FIG. 14). The drill stop 302 can include a housing 320 and a trigger 322. It should be noted that although the housing 320 and trigger 322 are illustrated and described herein as separate, discrete components, the housing 320 and trigger 322 could be integrally formed, if desired.

With reference to FIGS. 15 and 16, the housing 320 can be generally cylindrical, and can include a proximal end 324, a distal end 326 and a throughbore 328 (FIG. 16), which can extend from the proximal end 324 to the distal end 326. The proximal end 324 can be configured to contact, but not pass through, the soft tissue sleeves 208 of the guide wire system 26 (FIG. 10). Thus, the proximal end 324 can generally have a diameter that is larger than the diameter of the outer soft tissue sleeve 208*b* to stop the advancement of the drill bit 300 into the anatomy.

With reference back to FIGS. 15 and 16, the distal end 326 can include a trigger slot 330 and one or more flanges 332. The trigger slot 330 can be sized to enable the trigger 322 to fit within the housing 320, and thus, in one example, the trigger slot 330 can include a first portion 330*a* and a second portion 330*b*, as shown in FIG. 16. The first portion 330*a* can generally be wider than the second portion 330*b*, and can be sized such that the trigger 322 extends beyond a surface of the housing 320 when the trigger 322 is in a first, locked position. In a second, unlocked position, the trigger 322 can generally be about planar with the surface of the housing 320. The second portion 330*b* can extend beyond the throughbore 328 to enable the trigger 322 to engage the drill bit 300, as will be discussed. The second portion 330*b* can also include a generally flat portion 330*c*. As will be discussed, the trigger 322 can be biased against the flat portion 330*c* between the first, locked position and the second, unlocked position.

The flanges 332 can project from the distal end 326. The flanges 332 can include about three flanges 332*a-c*, spaced about equally apart, however, any number of flanges 332 could be formed at the distal end 326, such as two flanges 332. Typically, as best illustrated in FIG. 10, at least two of the flanges 332 can provide a window through which the surgeon can view the depth label 314*b* of the drill bit 300. This can enable the surgeon to align the housing 320 so that the desired depth for the drill bit 300 as indicated by the depth marker 314 is viewable between two of the flanges 332.

With reference back to FIG. 16, the throughbore 328 of the housing 320 can be sized to enable the drill bit 300 to pass through the housing 320. Generally, the throughbore 328 can be sized such that at least the proximal end 304 and the intermediate portion 306 of the drill bit 300 can pass through the housing 320.

With reference to FIGS. 10, 14 and 17, the trigger 322 can be received within the trigger slot 330 of the housing 320, and can be operable to enable the surgeon to select the desired depth for the drill bit 300, via the engagement of the trigger 322 with the depth markers 314. In this regard, with reference to FIG. 17, the trigger 322 can include a button 340, a bore 342 and a biasing element 344, which can cooperate with the housing 320 and the depth markers 314 to limit the advancement of the drill bit 300 to the selected depth. Generally, the button 340, the bore 342 and the biasing element 344 can be integrally formed into one-piece, however, each of the button 340, the bore 342 and the biasing element 344 could comprise discrete elements, if desired.

The button 340 can be generally rectangular, and comprise a surface for receipt of a user-input. The bore 342 can be formed between the button 340 and the biasing element 344, and can be sized so that the intermediate portion 306 of the drill bit 300 can pass through the trigger 322 when the trigger 322 is in the second, unlocked position. The biasing element 344 can comprise any suitable element capable of providing a biasing force against the flat portion 330*c* of the trigger slot 330, such as a spring. In one example, the biasing element 344 can comprise a leaf spring, which can include a biasing arm 344*a*. The biasing arm 344*a* can apply the biasing force against the flat portion 330*c* to enable the trigger 322 to move between the first, locked position and the second, unlocked position (FIG. 14).

In this regard, with reference to FIG. 14, with the trigger 322 assembled to the housing 320, the biasing arm 344*a* biases the trigger 322 above the surface of the housing 320. When the trigger 322 extends beyond the surface of the housing 320, the bore 342 is not coaxial with the throughbore 328, and thus, the drill bit 300 cannot pass through the drill stop 302. Further, at least an edge of the bore 342 can engage the groove 314*a* to secure the drill stop 302 to the drill bit 300. When the trigger 322 is biased downward, in the second, unlocked position toward the housing 320, the biasing arm 344*a* can move so that the bore 342 of the trigger 322 can be coaxially aligned with the throughbore 328. When the bore 342 is coaxially aligned with the housing 320, the drill bit 300 can move within the drill stop 302, which can enable the user to select the desired depth for the drill bit 300 to traverse, by aligning the desired depth marker 314 between at least two of the flanges 332 (FIG. 10).

Thus, the drill system 30 can be employed with the guide wire system 26 to enable a user, such as a surgeon, to advance the drill bit 300 to a desired depth within the anatomy, selected via the drill stop 302, in order to prepare the anatomy for receipt of one or more fasteners, such as the reconstructive screws 18.

Reconstructive Screws

Figure 18:
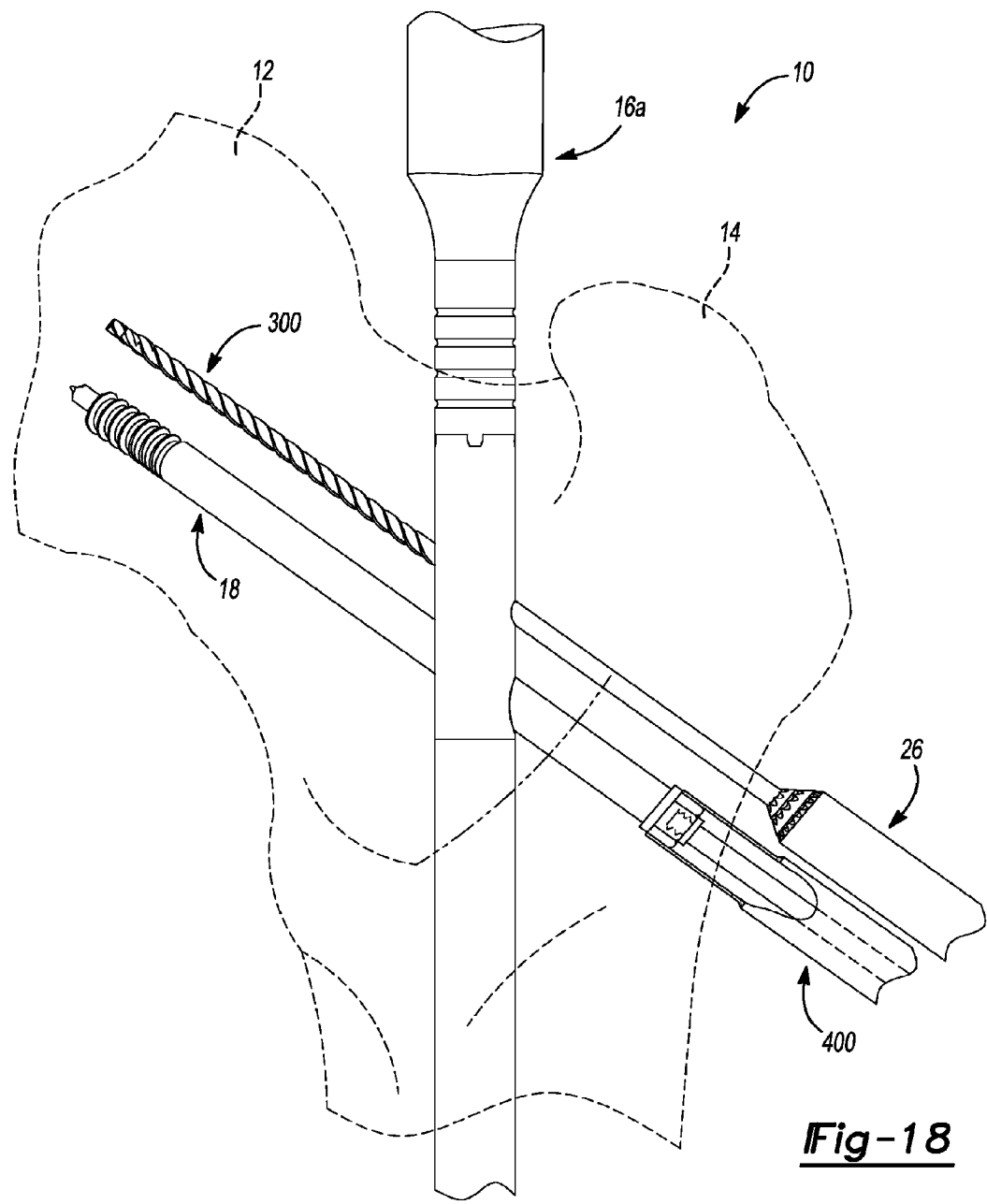
FIG. 18 is a schematic environmental illustration of the first guide instrument including a first exemplary orthopedic fastener, such as a first exemplary orthopedic screw, according to the present teachings.

With reference to FIG. 18, according to various teachings, each of the reconstructive screws 18 can comprise a first exemplary reconstructive screw 18a or a second exemplary reconstructive screw 18b, as will be discussed. The second exemplary reconstructive screw 18b can be configured to engage various drivers to facilitate the easy removal of the second exemplary reconstructive screw 18b, if desired. Generally, the reconstructive screws 18 can be inserted into an anatomy prepared by the drill system 30 over the guide wire system 26, however, any appropriate technique could be used to insert the reconstructive screws 18.

First Exemplary Reconstructive Screw

Figure 19:
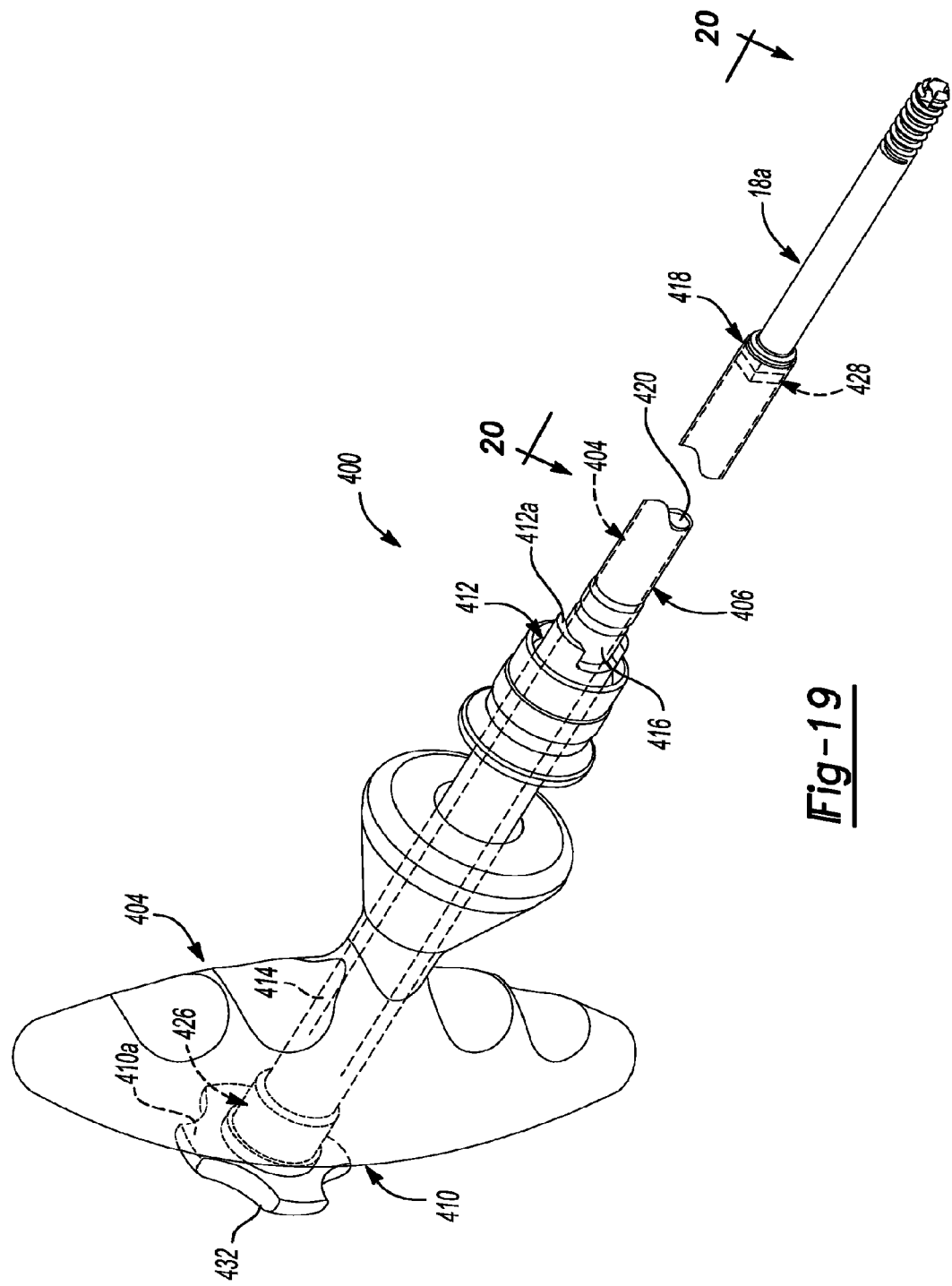
FIG. 19 is a schematic environmental illustration of an exemplary screw insertion instrument including a first exemplary orthopedic screw according to the present teachings.

With reference to FIG. 19, in one example, a screw insertion instrument 400 can be used to implant each of the orthopedic screws 18a into the anatomy, as will be discussed below. The screw insertion instrument 400 can include a handle 402, an inserter 404, an elongated connecting member 406 and the reconstructive screw 18a. Each of the handle 402, inserter 404, elongated connecting member 406 and the reconstructive screw 18a can be formed of a sterilizable material, and typically each can be formed of a biocompatible material, such as a metal, metal alloy, polymer or combinations thereof.

The handle 402 can enable a user, such as a surgeon, to insert the reconstructive screw 18a into an anatomy. As the handle 402 can comprise any suitable graspable or manipulable portion, the handle 402 will not be discussed in great detail herein. Briefly, however, the handle 402 can include a first end 410, a second end 412 and a throughbore 414. The first end 410 can define a recess 410a that can couple the elongated connecting member 406 to the handle 402, via a press-fit or a keyed fit, for example. The second end 412 can include a projection 412a that is sized to couple the handle 402 to the inserter 404, and the projection 412a can include internal threads, a taper or other equivalent features to enable the inserter 404 to be removably coupled to the handle 402. The throughbore 414 can pass through the recess 410a and projection 412a to enable the elongated connecting member 406 to pass through the handle 402 and into the inserter 404.

Figure 20:
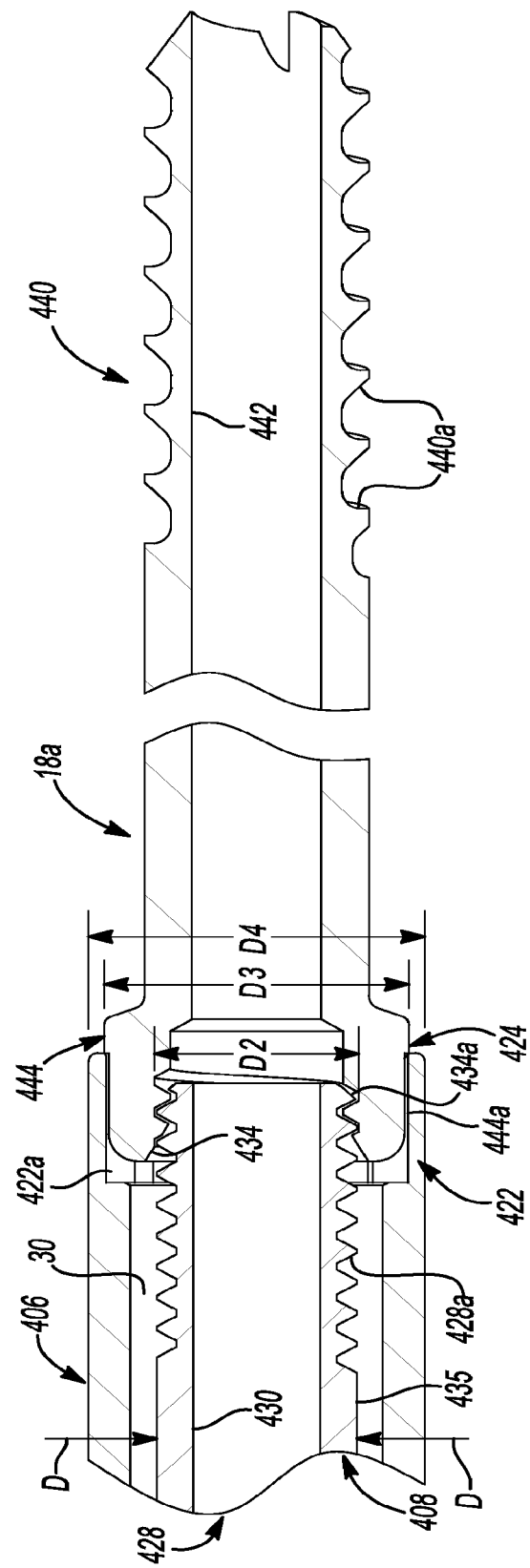
FIG. 20 is a partial cross-sectional view of the screw insertion instrument including the first exemplary orthopedic screw taken along line 20-20 of FIG. 19.

With reference to FIGS. 19 and 20, the inserter 404 can include a first end 416, a second end 418 and a throughbore 420. The inserter 404 can enable the surgeon to apply a manual torque to the reconstructive screw 18a to drive the reconstructive screw 18a into an anatomy. The first end 416 of the inserter 404 can be coupled to the second end 412 of the handle 402, and can include mating threads, a mating taper, or other equivalent features to couple the handle 402 to the inserter 404. Alternatively, a surgeon can couple a powered tool, such as a drill, to the insert 404 to drive the screws 18 into the anatomy. The second end 418 can be coupled to the reconstructive screw 18a. In one aspect, for example, and with reference to FIG. 20, the second end 418 can include a formed interior surface 422 formed about a portion of the throughbore 420 that can be configured to mate with the reconstructive screw 18a. In one aspect, the interior surface 422 can include a formed hexagonal surface 422a that is sized to mate with a head 424 of the reconstructive screw 18a, as will be discussed below, to couple the reconstructive screw 18a to the inserter 404. It should be understood, however, that the interior surface 422 can have any desired shape to mate with the head 424, such as notched, keyed, grooved, annular, polygonal, etc. The throughbore 420 can be formed from the first end 416 to the second end 418. The throughbore 420 can be sized to enable the elongated connecting member 406 to move relative to the inserter 404. In this regard, the throughbore 420 can be sized to enable the elongated connecting member 406 to slide and rotate relative to the inserter 404, as will be discussed herein.

Figure 22:
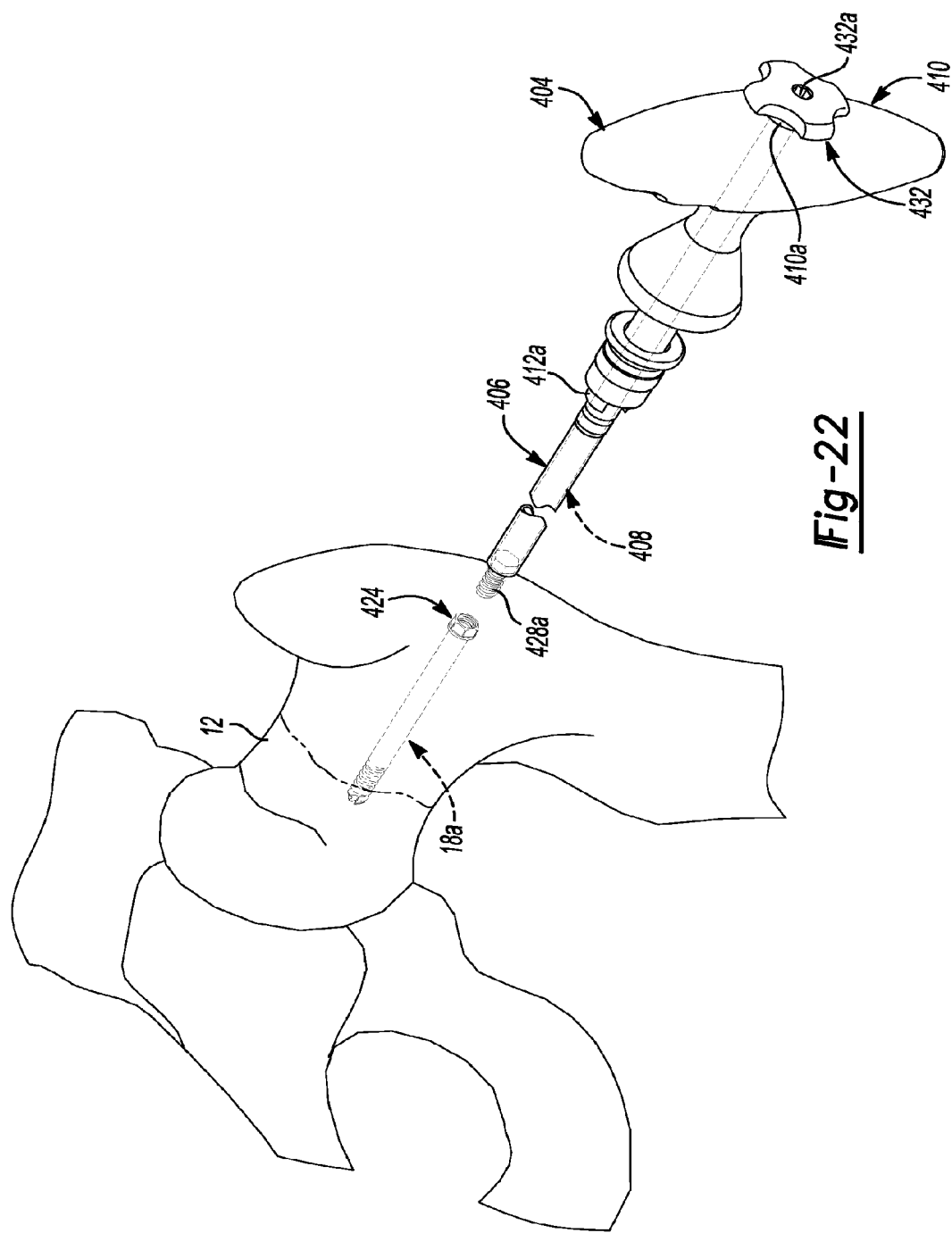
FIG. 22 is an schematic environmental illustration showing the insertion of the first exemplary orthopedic screw into the anatomy.

With reference to FIGS. 19 and 20, the elongated connecting member 406 can be slideably received within the inserter 404 in the case that the inserter 404 is employed with the handle 402 in a manual method. The elongated connecting member 406 can couple the reconstructive screw 18a to the handle 402 so that the manual torque generated by the rotation of the handle 402 and transferred to the inserter 404 can drive the reconstructive screw 18a into an anatomy. The elongated connecting member 406 can include a first end 426, a second end 428 and a throughbore 430. The first end 426 can include a graspable portion 432. The graspable portion 432 can be coupled to the first end 426 via any suitable technique, such as a press fit, mechanical fasteners, or other equivalent features, or could be integrally formed with the first end 426. The graspable portion 432 can enable the surgeon to insert the elongated connecting member 406 through the handle 402 and inserter 404, and can couple the elongated connecting member 406 to the handle 402 as shown in FIG. 22. The graspable portion 432 can also include a bore 432a that can be aligned with the throughbore 430 of the elongated connecting member 406 to enable the elongated connecting member 406 to pass over a guide wire (not specifically shown), for example.

With reference to FIG. 20, the second end 428 can be configured to couple the reconstructive screw 18a to the elongated connecting member 406. In this regard, the second end 428 can include a plurality of threads, a keyed projection, a notch, etc. configured to mate with an internal surface 434 of the head 424 of the reconstructive screw 18a, as will be discussed. In the example of FIG. 20, the second end 428 includes a plurality of threads 428a formed on an exterior surface 435 of the elongated connecting member 406. The throughbore 430 can enable the elongated connecting member 406 to be positioned over a guide wire (not specifically shown), for example, which can ensure the proper positioning of the reconstructive screw 18a with respect to an anatomy.

Figure 21:
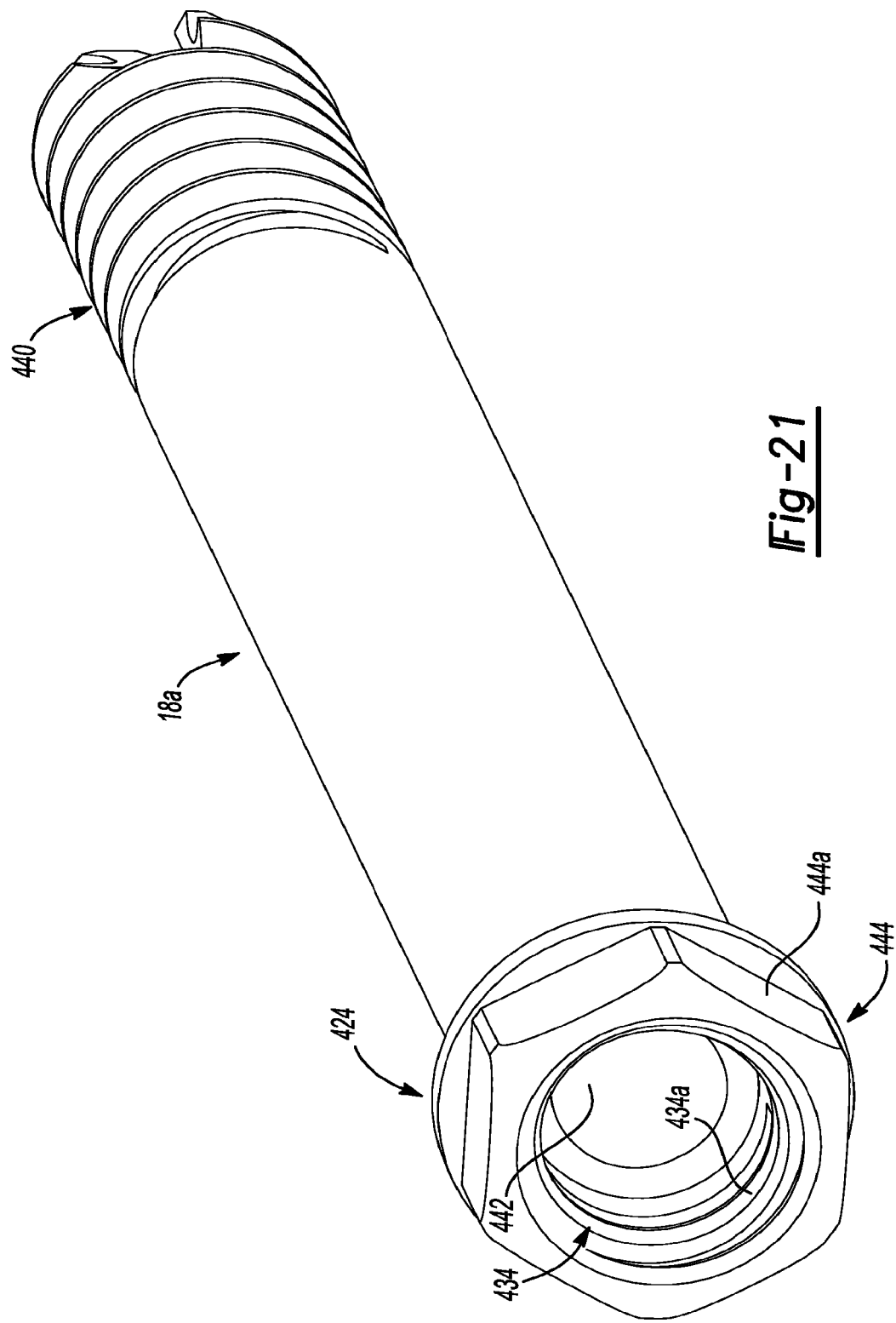
FIG. 21 is a detail view of the first exemplary orthopedic screw of FIG. 19.

The reconstructive screw 18a can be used to repair one or more portions of an anatomy, and for example, as illustrated in FIG. 22, the reconstructive screw 18a can be used to repair a fracture in the femoral head 12. The reconstructive screw 18a can be coupled to the elongated connecting member 406, and can be driven by the inserter 404 by torque applied to the handle 402 into an anatomy, such as the femoral head 12. The reconstructive screw 18a can be composed of a biocompatible material, such as a metal, metal alloy or polymer, and if desired, can comprise a coating, such as an antibiotic coating, a coating to enhance bone ingrowth, etc. With reference to FIGS. 20 and 21, the reconstructive screw 18a can include a first end or the head 424, a second end or a fastening portion 440 and a throughbore 442.

The head 424 can be sized to enable the reconstructive screw 18a to receive torque from the inserter 404, while enabling the reconstructive screw 18a to be coupled to the elongated connecting member 406. The head 424 can include a first or exterior surface 444 and a second or the internal surface 434. The exterior surface 444 can be configured to mate with the second end 418 of the inserter 404. In this example, the exterior surface 444 can comprise a hexagonal surface 444a, however, it will be understood that the exterior surface 444 can have any desired shape to enable the inserter 404 to apply a torque to the reconstructive screw 18a, such as annular, ridged, ribbed, polygonal, grooved, notched, dimpled, slotted, keyed, or other equivalent features.

The internal surface 434 can be configured to mate with the second end 428 of the elongated connecting member 406 to releasably couple the reconstructive screw 18a to the elongated connecting member 406. Thus, the internal surface 434 can have any desired shape, such as grooved, notched, slotted, dimpled, keyed, polygonal, etc. For example, the internal surface 434 can include a plurality of threads 434a that can mate with the threads 428a on the second end 428 of the elongated connecting member 406 (FIG. 20). By configuring the internal surface 434 to mate with the elongated connecting member 406, a diameter D of the elongated connecting member 406 can be reduced, as the diameter of the elongated connecting member 406 can be sized to mate with a diameter D2 of the internal surface 434, instead of a diameter D3 of the exterior surface 444, for example. By reducing the diameter D of the elongated connecting member 406, a diameter D4 of the inserter 404 can also be reduced. In addition, by using the internal surface 434 of the head 424 to couple the reconstructive screw 18a to the elongated connecting member 406, a diameter D5 of the reconstructive screw 18a can be reduced. Thus, the use of the internal surface 434 of the head 424 to couple the reconstructive screw 18a to the elongated connecting member 406 can serve to reduce the size of the screw insertion instrument 400.

The fastening portion 440 of the reconstructive screw 18a can define at least one fastening feature that can couple the reconstructive screw 18a to an anatomy. For example, the fastening portion 440 can comprise one or more threads 440a, as illustrated, however, it should be noted that the fastening portion 440 can comprise any suitable fastening feature, such as a taper, barbs, etc. If the fastening portion 440 comprises the threads 440a, then the threads 440a can be self-tapping and self-drilling to enable the reconstructive screw 18a to be coupled to an anatomy without necessarily requiring the formation of a pre-tapped bore in an anatomy. The throughbore 442 can be sized to enable the reconstructive screw 18a to slideably engage a guide wire (not specifically shown), or to enable other instruments (not shown) to be inserted into an anatomy via the screw insertion instrument 400.

With reference to FIG. 22, the screw insertion instrument 400 can be used to drive the reconstructive screw 18a into an anatomy, such as the femoral head 12. In order to drive the reconstructive screw 18a into the anatomy, the first end 416 of the inserter 404 can be coupled to the second end 412 of the handle 402. Then, the elongated connecting member 406 can be inserted through the throughbore 414 of the handle 402 and the throughbore 420 of the inserter 404. The reconstructive screw 18a can be coupled to the second end 418 of the inserter 404 such that the interior surface 422 of the inserter 404 can be coupled to the exterior surface 444 of the head 424. With the reconstructive screw 18a coupled to the inserter 404, the graspable portion 432 of the elongated connecting member 406 can be manipulated to couple the internal surface 434 of the head 424 of the reconstructive screw 18a to the second end 428 of the elongated connecting member 406. For example, if the internal surface 434 comprises the plurality of threads 434a, then the elongated connecting member 406 can be rotated by the user, such as the surgeon, to couple the plurality of threads 428a of the elongated connecting member 406 to the plurality of threads 434a of the reconstructive screw 18a.

With the reconstructive screw 18a coupled to the elongated connecting member 406 and the inserter 404, the surgeon can place the screw insertion instrument 400 about a selected guide wire 202, 204 and can guide the reconstructive screw 18a into a desired position in an anatomy such as the femoral head 12. Once positioned, the surgeon can rotate the handle 402 to drive the reconstructive screw 18a into an anatomy, such as the femoral head 12. When the reconstructive screw 18a is secured in the femoral head 12, the surgeon can then manipulate the elongated connecting member 406, via the graspable portion 432, to release the elongated connecting member 406 from the reconstructive screw 18a. The screw insertion instrument 400 can then be removed from the anatomy.

Second Exemplary Reconstructive Screw

Figure 25:
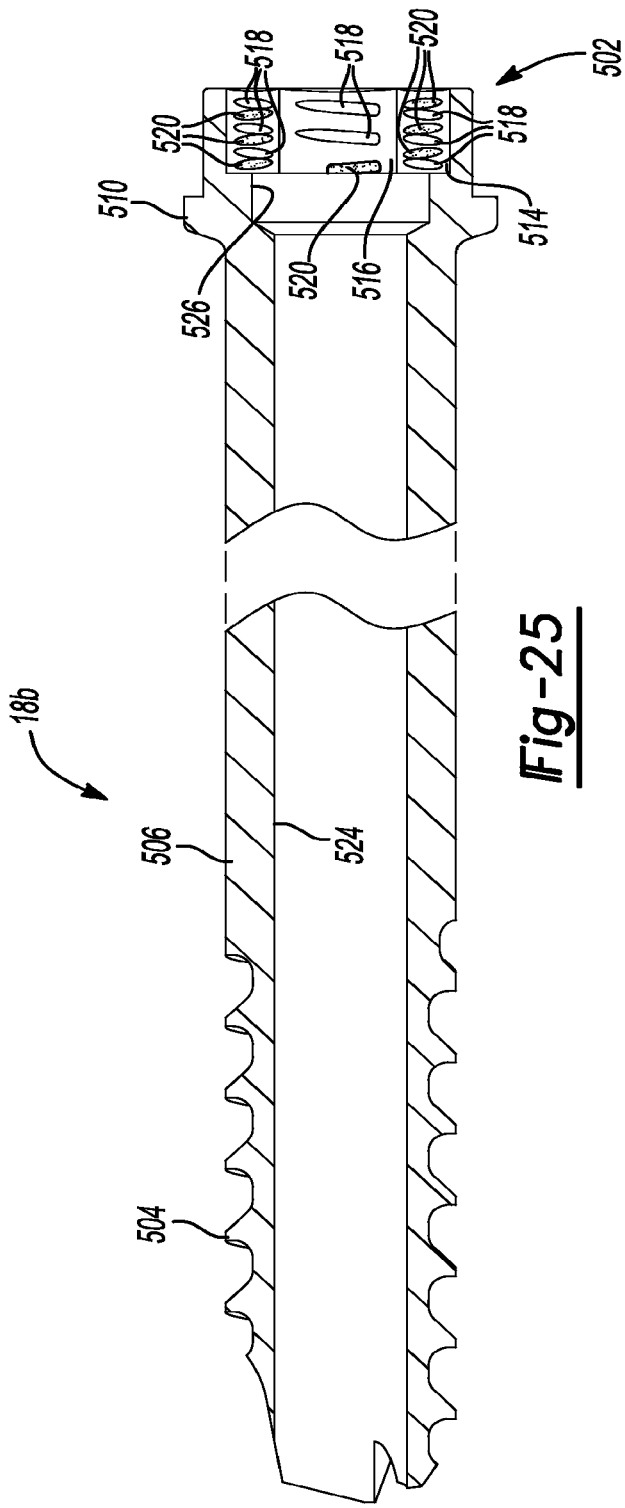
FIG. 25 is a longitudinal sectional view of the second exemplary orthopedic screw of FIG. 23.

Referring to FIGS. 23-25, a second exemplary reconstructive screw 18b according to the present teachings can include a head 502, an unthreaded shank portion 506, and an externally threaded anchoring portion 504 for engaging bone or other tissue. The head 502 can include a cylindrical base 510 and a male or outer hex wall 512 extended from the cylindrical base 510 away from the shank portion 506. The reconstructive screw 18b can be cannulated to define an axial internal through bore of stepwise variable diameters, including a shank bore 524 and first and second head bores 514, 526, as shown in FIG. 25.

Referring to FIGS. 23-25, the head 502 can include a female or inner hexagonal socket surface or inner hex surface 516, on which a female right handed thread 518 and a female left handed thread 520 are defined. As a practical matter, each of the right handed and left handed threads 518, 520 can be formed on the inner surface of the first inner head bore 514, which is cylindrical before the inner hex surface 516 is cut. The inner hex surface 516 can be formed after the right handed and left handed threads 518, 520 are defined, thereby partially interrupting the threads 518, 520, such that the right handed thread 518 and a left handed thread 520, which are deeper than the inner hex surface 516, are still defined on the sides of the inner hex surface 516. Although the thread area is reduced, sufficient thread area is maintained, such that both the right handed and left handed threads 518, 520 remain functional.

Accordingly, the head 502 of the reconstructive screw 18b provides the following concurrent and overlapping driver interface features, which can be used selectively for interfacing with an appropriate driver for inserting and/or removing the reconstructive screw 18b from bone or other tissue:

A. an outer (male) hex surface 512 defined on the outer surface of the head 502;

B. an inner (female) right handed thread 518 defined on the first inner head bore 514;

C. an inner (female) left handed thread 520 defined on the first inner head bore 514; and D. an inner (female) hex surface 516 defined on the first inner head bore 514.

The above driver interface features allow the use of commonly available hex drivers, or socket drivers, or threaded engagement drivers. Other specialized or dedicated drivers can also be used, as discussed below.

Figure 26:
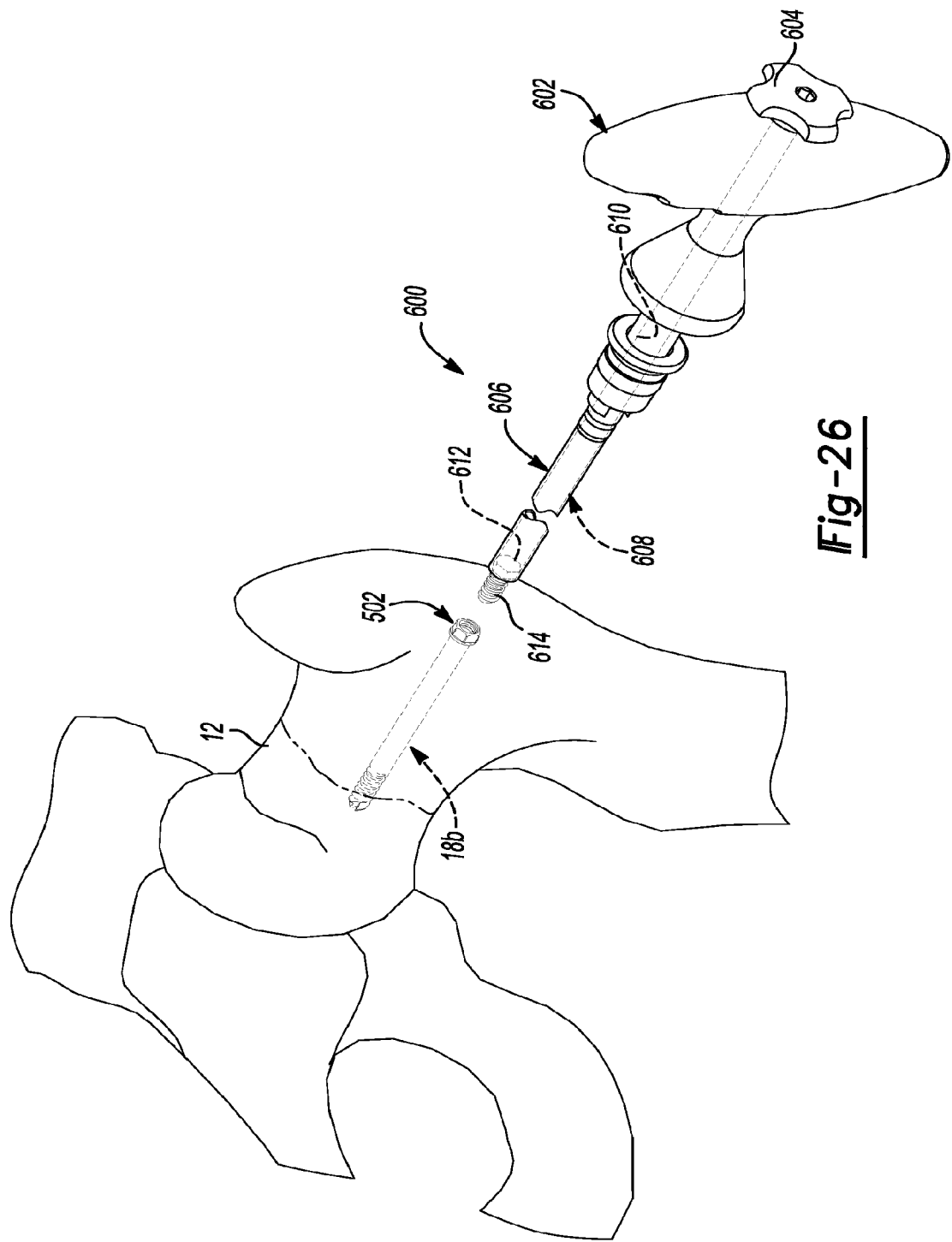
FIG. 26 is a perspective environmental view showing the second exemplary orthopedic screw of FIG. 23 with a first driver.

Referring to FIG. 26, a first driver 600 can be used to insert and/or remove the reconstructive screw 18b in or out of the anatomy, such as a femoral head 12. The first driver 600 can generally include a handle 602 and a cannulated inserter shaft 606 passing through the handle 602 and having an inner longitudinal bore 610 and a distal inner (female) hex socket or surface 612. The first driver 600 can also include a connecting member 608 received through the bore 610 and having an outer (male) threaded distal end 614 and a proximal end coupled to a knob or other holding member 604. The holding member 604 can be accessible outside the handle 602 for rotating the connecting member 608. The inner hex surface 612 can be engaged with the outer hex surface 512 of the head 502 of the reconstructive screw 18b, and rotated clockwise or counterclockwise to insert or remove the reconstructive screw 18b into or out of the femoral head 12. The threaded distal end 614 of the connecting member 608 can be threadably engaged to the right handed thread 518 of the inner head bore 514 by turning the holding member 604. The threaded engagement of the connecting member 608 and the reconstructive screw 18b can stabilize the reconstructive screw 18b while inserting or removing the reconstructive screw 18b from the femoral head 12.

Referring to FIGS. 27-29, a second driver 700 can be used to inset and/or remove the reconstructive screw 18b. The second driver 700 can include a cannulated shaft 706 having an inner longitudinal bore 704 and a distal end defining an outer (male) hex surface 702. The outer hex surface 702 of the second driver 700 can engage the inner hex surface 516 of the head 502 of the reconstructive screw 18b. Rotating the second driver 700 clockwise or counterclockwise can insert or remove the reconstructive screw 18b.

Referring to FIGS. 30-32, a third driver 800 can be used to remove the reconstructive screw 18b. The third driver 800 can include a cannulated shaft 806 having an inner longitudinal bore 804 and a distal end defining a male left handed thread 802. The male left handed thread 802 can engage the female left handed thread 520 of the first inner head bore 514 of the reconstructive screw 18b. After the male left handed thread 802 is fully engaged to the female left handed thread 520 and the third driver 800 has reached the step surface between the first and second head bores 514, 526, the third driver 800 can be rotated counterclockwise to remove the reconstructive screw 18b from the femoral head 12, while the third driver 800 remains fully engaged to the reconstructive screw 18b by the engagement of the respective left handed threads 802 and 520.

Additionally, an ordinary driver similar to the third driver 800 but with a right handed thread can be used to insert the reconstructive screw 18b, if no other appropriate driver is available.

It will be appreciated that the reconstructive screw 18b incorporates several driver interface features associated with the head 502 of the reconstructive screw 18b. Depending on the available drivers, one or more of these features can be selectively engaged with the available driver to insert or remove the reconstructive screw 18b, as described above. Accordingly, when the primary insertion or removal tool that is associated with the reconstructive screw 18b is not available during the procedure, alternative and more commonly available drivers, such as hex drivers can be used.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A dual reconstructive wire system for use with an anatomy comprising:
   a first guide wire having a first end and a second end, the first end of the first guide wire operable to engage the anatomy, and the second end extending outside the anatomy;
   a second guide wire having a first end and a second end, the first end of the second guide wire operable to engage the anatomy, and the second end extending outside the anatomy;
   a first guide instrument having an intramedullary nail engagement feature and a guide that defines a first aperture and a second aperture;
   a first cannulated insertion instrument having a first end configured to be inserted into the anatomy, and a second end configured to extend beyond the anatomy, with at least a portion of the first cannulated insertion instrument received through one of the first aperture or the second aperture;
   a second cannulated insertion instrument having a first end configured to be inserted into the anatomy, and a second end configured to extend beyond the anatomy, with at least a portion of the second cannulated instrument received through the other of the first aperture or the second aperture; and
   a retrograde intramedullary nail;
   wherein the first guide wire passes through the first cannulated insertion instrument such that the first end and the second end of the first guide wire extend beyond the first end and the second end, respectively, of the first cannulated insertion instrument, and the second guide wire passes through the second cannulated insertion instrument such that the first end and the second end of the second guide wire extend beyond the first end and the second end, respectively, of the second cannulated insertion instrument, and
   wherein the first guide instrument engages the retrograde intramedullary nail.

2. The system of claim 1, wherein the guide comprises:
   a first arm having a proximal end including the intramedullary nail engagement feature therein and a distal end; and
   a second arm coupled to the distal end of the first arm and defining the first and second apertures.

3. The system of claim 2, wherein the guide further defines a third aperture and a fourth aperture.

4. The system of claim 2, further comprising a fastener that removably couples the first and second arms.

5. The system of claim 1, wherein the first guide wire has a colored coating to visually distinguish the first guide wire from the second guide wire.

6. The system of claim 1, further comprising at least one radio-opaque marker disposed in the guide.

7. The system of claim 1, wherein the first guide instrument is substantially U-shaped.

8. The system of claim 1, wherein the first cannulated insertion instrument and the second cannulated insertion instrument each include a trocar and at least two soft tissue sleeves.

9. The system of claim 8, wherein at least one of the at least two soft tissue sleeves has a stop contacting the first guide instrument, the trocar operable to penetrate a soft tissue of the anatomy, with a first one of the at least two soft tissue sleeves slideable over the trocar and having a diameter larger than the trocar to create a passageway through the anatomy, and a second one of the at least two soft tissue sleeves having a second diameter larger than the diameter of the first one of the at least two soft tissue sleeves, the second one of the at least two soft tissue sleeves slideable over the first one of the at least two soft tissue sleeves to increase the diameter of the passageway formed by the first one of the at least two soft tissue sleeves in the anatomy.

10. The system of claim 9, wherein the passageway formed by the first one of the at least two soft tissue sleeves through the soft tissue terminates adjacent to boney tissue in the anatomy.

11. The system of claim 1, further comprising:
a gage including a first scale and a second scale, the gage defining a single bore, receiving the second end of the first guide wire, which extends beyond the first cannulated insertion instrument to measure a depth of the first guide wire within the anatomy with the first scale, and receives the second end of the second guide wire, which extends beyond the second cannulated insertion instrument to measure a depth of the second guide wire within the anatomy with the second scale.

12. The system of claim 8, wherein the first cannulated insertion instrument and the second cannulated insertion instrument each include a stop mating with the first guide instrument to limit advancement of the first cannulated instrument and second cannulated instrument through the first aperture and second aperture, respectively.

13. A dual reconstructive wire system for use with an anatomy comprising:
a first guide wire having a first end and a second end, the first end of the first guide wire operable to engage the anatomy, the second end operable to extend outside the anatomy;
a second guide wire having a first end and a second end, the first end of the second guide wire operable to engage the anatomy, the second end operable to extend outside the anatomy;
a first U-shaped guide instrument having an intramedullary nail engagement feature on a first end and a guide on an opposite end, the guide defining a first aperture and a second aperture, the first U-shaped guide instrument including two independent and selectively attachable arms;
a first cannulated insertion instrument having a first end operable to be inserted into the anatomy with at least a portion of the first cannulated instrument received through one of the first aperture or the second aperture; and
a second cannulated insertion instrument having a first end operable to be inserted into the anatomy with at least a portion of the second cannulated instrument received through the other of the first aperture or the second aperture;
wherein the first cannulated insertion instrument and the second cannulated insertion instrument each include a trocar and at least two soft tissue sleeves, and
wherein at least one of the at least two soft tissue sleeves has a stop that contacts the first guide instrument, the trocar operable to penetrate a soft tissue of the anatomy, with a first one of the at least two soft tissue sleeves slideable over the trocar and having a diameter larger than the trocar to create a passageway through the anatomy, and a second one of the at least two soft tissue sleeves having a second diameter larger than the diameter of the first one of the at least two soft tissue sleeves, the second one of the at least two soft tissue sleeves slideable over the first one of the at least two soft tissue sleeves to increase the diameter of the passageway formed by the first one of the at least two soft tissue sleeves in the anatomy.

14. The system of claim 13, wherein the two independent arms comprise:
a first arm having a proximal end including the intramedullary nail engagement feature therein and a distal end; and
a second arm that is coupled to the distal end of the first arm and defines the first and second apertures.

15. The system of claim 14, further comprising a fastener removably coupling the first and second arms.

16. The system of claim 1, wherein the intramedullary nail engagement feature includes a bolt configured to threadably engage the retrograde intramedullary nail.

17. The system of claim 16, further comprising a driver nose supported by the first guide instrument, the driver nose including a bore, wherein the bolt is disposed within the bore of the driver nose.

18. A dual reconstructive wire system for use with an anatomy comprising:
a first guide wire having a first end and a second end, the first end of the first guide wire operable to engage the anatomy, and the second end extending outside the anatomy;
a second guide wire having a first end and a second end, the first end of the second guide wire operable to engage the anatomy, and the second end extending outside the anatomy;
a first guide instrument having an intramedullary nail engagement feature and a guide that defines a first aperture and a second aperture;
a first cannulated insertion instrument having a first end configured to be inserted into the anatomy, and a second end configured to extend beyond the anatomy, with at least a portion of the first cannulated insertion instrument received through one of the first aperture or the second aperture; and
a second cannulated insertion instrument having a first end configured to be inserted into the anatomy, and a second end configured to extend beyond the anatomy, with at least a portion of the second cannulated instrument received through the other of the first aperture or the second aperture;
wherein the first guide wire passes through the first cannulated insertion instrument such that the first end and the second end of the first guide wire extend beyond the first end and the second end, respectively, of the first cannulated insertion instrument, and the second guide wire passes through the second cannulated insertion instrument such that the first end and the second end of the second guide wire extend beyond the first end and the second end, respectively, of the second cannulated insertion instrument, wherein the first cannulated insertion instrument and the second cannulated insertion instrument each include a trocar and at least two soft tissue sleeves, and wherein at least one of the at least two soft tissue sleeves has a stop contacting the first guide instrument, the trocar operable to penetrate a soft tissue of the anatomy, with a first one of the at least two soft tissue sleeves slideable over the trocar and having a diameter larger than the trocar to create a passageway through the anatomy, and a second one of the at least two soft tissue sleeves having a second diameter larger than the diameter of the first one of the at least two soft tissue sleeves, the second one of the at least two soft tissue sleeves slideable over the first one of the at least two soft tissue sleeves to increase the diameter of the passageway formed by the first one of the at least two soft tissue sleeves in the anatomy.

19. The system of claim 13, wherein the first guide wire passes through the first cannulated insertion instrument such that the first end and the second end of the first guide wire extend beyond the first end and the second end, respectively, of the first cannulated insertion instrument, and the second guide wire passes through the second cannulated insertion instrument such that the first end and the second end of the second guide wire extend beyond the first end and the second end, respectively, of the second cannulated insertion instrument.

* * * * *